(12) United States Patent
Morita

(10) Patent No.: US 11,961,165 B2
(45) Date of Patent: Apr. 16, 2024

(54) TOMOGRAPHIC IMAGE GENERATING APPARATUS, TOMOGRAPHIC IMAGE GENERATING METHOD, AND TOMOGRAPHIC IMAGE GENERATING PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 478 days.

(21) Appl. No.: 17/169,564

(22) Filed: Feb. 8, 2021

(65) Prior Publication Data

US 2021/0166443 A1 Jun. 3, 2021

Related U.S. Application Data

(63) Continuation of application No. PCT/JP2019/038261, filed on Sep. 27, 2019.

(30) Foreign Application Priority Data

Sep. 27, 2018 (JP) .................................. 2018-182724

(51) Int. Cl.
*G06T 11/00* (2006.01)
*A61B 6/00* (2006.01)
(Continued)

(52) U.S. Cl.
CPC ............ *G06T 11/005* (2013.01); *A61B 6/025* (2013.01); *A61B 6/4429* (2013.01);
(Continued)

(58) Field of Classification Search
CPC .................. G06T 11/005; G06T 7/0012; G06T 2207/10112; G06T 2207/30068;
(Continued)

(56) References Cited

U.S. PATENT DOCUMENTS

2009/0123052 A1 5/2009 Ruth et al.
2016/0081644 A1 3/2016 Fukuda
(Continued)

FOREIGN PATENT DOCUMENTS

EP 3586750 A1 1/2020
EP 3590431 A1 1/2020
(Continued)

OTHER PUBLICATIONS

Extended European Search Report dated Oct. 19, 2021, issued in corresponding EP Patent Application No. 19867935.9.
(Continued)

*Primary Examiner* — Edward F Urban
*Assistant Examiner* — Wassim Mahrouka
(74) *Attorney, Agent, or Firm* — SOLARIS Intellectual Property Group, PLLC

(57) ABSTRACT

An image acquisition unit acquires a plurality of projection images corresponding to a plurality of radiation source positions in a case of tomosynthesis imaging. A reconstruction unit reconstructs all or a part of the plurality of projection images to generate a tomographic image on each of a plurality of tomographic planes of a subject. A feature point detecting unit detects at least one feature point from a plurality of the tomographic images. A positional shift amount derivation unit derives a positional shift amount between the plurality of projection images with the feature point as a reference on a corresponding tomographic plane corresponding to the tomographic image in which the feature point is detected. The reconstruction unit reconstructs the plurality of projection images by correcting the positional shift amount to generate a corrected tomographic image.

18 Claims, 17 Drawing Sheets

(51) Int. Cl.
    *A61B 6/02*        (2006.01)
    *A61B 6/50*        (2024.01)
    *G06T 7/00*        (2017.01)

(52) U.S. Cl.
    CPC ............ *A61B 6/4452* (2013.01); *A61B 6/502* (2013.01); *G06T 7/0012* (2013.01); *G06T 2207/10112* (2013.01); *G06T 2207/30068* (2013.01); *G06T 2207/30168* (2013.01); *G06T 2211/40* (2013.01)

(58) Field of Classification Search
    CPC ... G06T 2207/40; A61B 6/025; A61B 6/4429; A61B 6/4452; A61B 6/502; A61B 6/032; A61B 6/0414; A61B 6/5205; A61B 6/5264; A61B 8/5223
    See application file for complete search history.

(56) References Cited

U.S. PATENT DOCUMENTS

| | | |
|---|---|---|
| 2016/0081645 A1 | 3/2016 | Fukuda |
| 2016/0095563 A1 | 4/2016 | Fukuda et al. |
| 2019/0149561 A1 | 5/2019 | Maeda et al. |

FOREIGN PATENT DOCUMENTS

| | | |
|---|---|---|
| EP | 3629295 A1 | 4/2020 |
| JP | 2014-128716 A | 7/2014 |
| JP | 2016-64118 A | 4/2016 |
| JP | 2016-64119 A | 4/2016 |
| JP | 2018-126969 A | 8/2018 |
| JP | 2018-182724 A | 11/2018 |
| JP | 2020-000313 A | 1/2020 |

OTHER PUBLICATIONS

English language translation of the following: Office action dated Mar. 29, 2022 from the JPO in a Japanese patent application No. 2020-549461 corresponding to the instant patent application.

International Search Report issued in International Application No. PCT/JP2019/038261 dated Dec. 17, 2019.

Written Opinion of the ISA issued in International Application No. PCT/JP2019/038261 dated Dec. 17, 2019.

Office Action dated May 3, 2023, issued by the EPO in corresponding EP Patent Application No. 19867935.9.

Office Action dated Feb. 16, 2024, issued by the EPO in corresponding EP Patent Application No. 19867935.9.

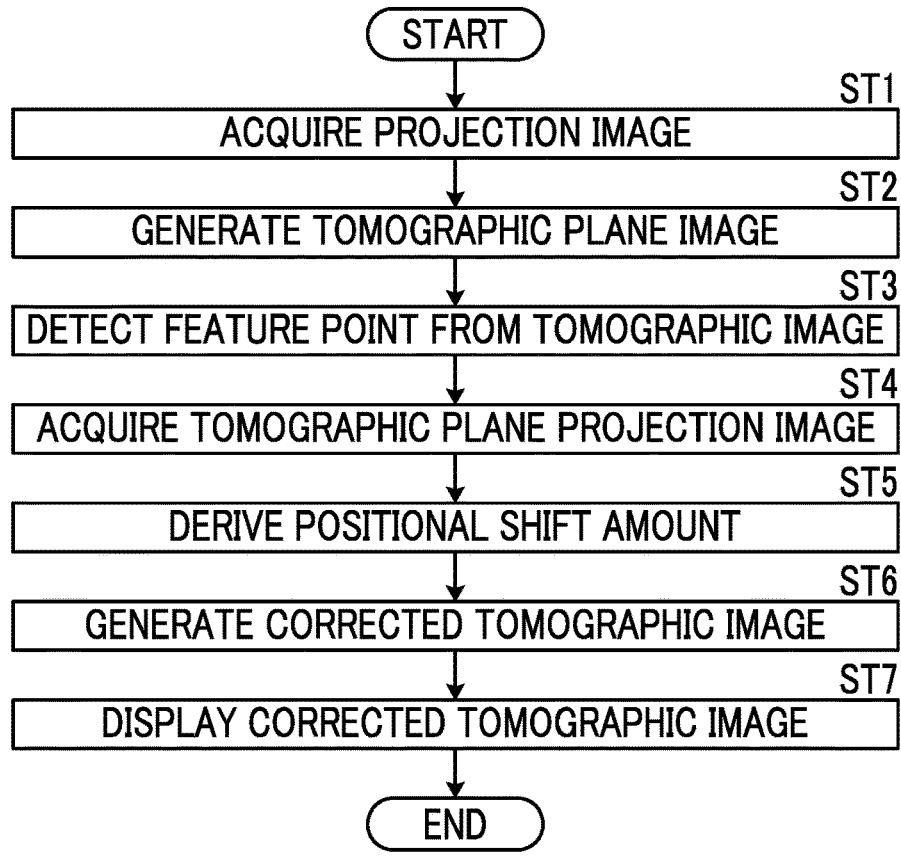
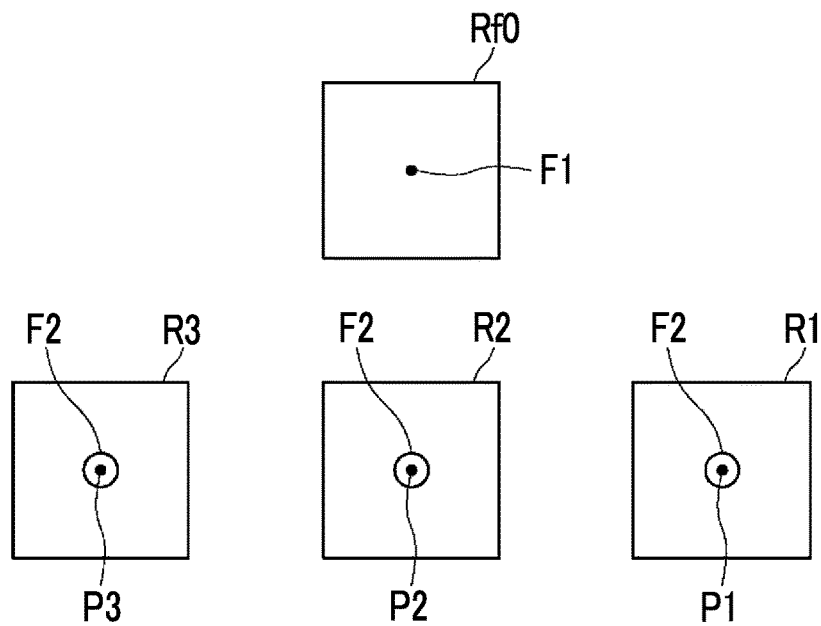

TOMOGRAPHIC IMAGE GENERATING APPARATUS, TOMOGRAPHIC IMAGE GENERATING METHOD, AND TOMOGRAPHIC IMAGE GENERATING PROGRAM

CROSS REFERENCE TO RELATED APPLICATIONS

The present application is a Continuation of PCT International Application No. PCT/JP2019/038261, filed on Sep. 27, 2019, which claims priority to Japanese Patent Application No. 2018-182724, filed on Sep. 27, 2018. Each of the above applications is hereby expressly incorporated by reference, in its entirety, into the present application.

BACKGROUND OF THE INVENTION

Technical Field

The present disclosure relates to a tomographic image generating apparatus, a tomographic image generating method, and a tomographic image generating program that acquire a plurality of projection images by imaging a subject at a plurality of radiation source positions to generate tomographic images from a plurality of projection images.

Related Art

In recent years, in radiation image capturing apparatuses using radiation such as X-rays and gamma rays, in order to observe an affected part in more detail, tomosynthesis imaging has been proposed in which imaging is performed by moving a radiation source to emit radiation to a subject from a plurality of radiation source positions and a plurality of projection images acquired by the imaging are added up to generate a tomographic image in which a desired tomographic plane is emphasized. In the tomosynthesis imaging, a plurality of projection images are acquired by imaging the subject at a plurality of radiation source positions by moving the radiation source in parallel to a radiation detector or moving the radiation source so as to draw a circular or elliptical arc according to the characteristics of the imaging apparatus and required tomographic images, and the projection images are reconstructed using, for example, a back projection method, such as a simple back projection method or a filtered back projection method, to generate a tomographic image.

By generating such a tomographic image on a plurality of tomographic planes of the subject, it is possible to separate structures overlapping each other in a depth direction in which the tomographic planes are aligned. Therefore, it is possible to find a lesion that has been difficult to detect in a two-dimensional image acquired by simple imaging in the related art. The simple imaging is an imaging method for acquiring one two-dimensional image, which is a transmission image of a subject, by emitting radiation to the subject once.

On the other hand, the tomosynthesis imaging has a problem that a reconstructed tomographic image is blurred due to the influence of body movement of the subject due to the time difference of imaging at the plurality of radiation source positions. In a case where the tomographic image is blurred as described above, it is difficult to find a lesion such as minute calcification, which is useful for early detection of breast cancer, particularly in a case where the breast is a subject.

For this reason, a method of correcting body movement in the case of generating a tomographic image from a projection image acquired by tomosynthesis imaging has been proposed. For example, JP2016-064119A discloses a method in which a plurality of tomographic plane projection images are acquired by projecting the pixel values of a plurality of projection images acquired by tomosynthesis imaging onto coordinate positions on a desired tomographic plane of a subject based on the positional relationship between the radiation source position and a radiation detector in a case of imaging the plurality of projection images while maintaining the pixel values of the plurality of projection images, feature points of an edge, the intersection of the edges, and the corner of the edge are detected in the plurality of tomographic plane projection images, positional shift between the plurality of tomographic plane projection images is corrected such that the detected feature points match, and a tomographic image is generated from the plurality of tomographic plane projection images subjected to positional shift correction.

On the other hand, the projection image acquired by tomosynthesis imaging is acquired by the radiation transmitted through the subject, and thus it is an image in which a plurality of structures in the subject overlap each other. Therefore, in a case where the position of the radiation source changes, the transmission direction of the radiation in the subject changes, and thus the appearance of feature points of the edge, the intersection of the edges, and the corner of the edge included in the projection image differs depending on the projection image. For example, a structure that appears as the intersection of edges in one projection image may appear as a plurality of edges that do not have an intersection in another projection image. As in the method disclosed in JP2016-064119A, in a case where the feature point detected in the tomographic plane projection image is used, the correspondence between the feature points cannot be accurately obtained, the accuracy of the correction of the positional shift, and thus a high-quality tomographic image may not be acquired.

SUMMARY OF THE INVENTION

The present disclosure has been made in view of the aforementioned circumstances, and is to make it possible to acquire a high-quality tomographic image in which the body movement is accurately corrected.

A tomographic image generating apparatus according to an aspect of the present disclosure comprises an image acquisition unit that acquires a plurality of projection images corresponding to a plurality of radiation source positions, the plurality of projection images being generated by causing an imaging apparatus to perform tomosynthesis imaging in which a radiation source is moved relative to a detection surface of a detection unit in order to emit radiation to a subject at the plurality of radiation source positions according to movement of the radiation source, a reconstruction unit that reconstructs all or a part of the plurality of projection images to generate a tomographic image on each of a plurality of tomographic planes of the subject, a feature point detecting unit that detects at least one feature point from a plurality of the tomographic images, and a positional shift amount derivation unit that derives a positional shift amount between the plurality of projection images based on body movement of the subject with the feature point as a reference on a corresponding tomographic plane corresponding to the tomographic image in which the feature point is detected, in which the reconstruction unit reconstructs the plurality of projection images by correcting the positional shift amount to generate a corrected tomographic image on at least one tomographic plane of the subject.

The "radiation source is moved relative to the detection unit" includes a case of moving only the radiation source, a case of moving only the detection unit, and a case of moving both the radiation source and the detection unit.

"Reconstruct all or a part of the plurality of projection images" means that reconstruction may be performed with all of the plurality of projection images, or reconstruction may be performed with two or more projection images among the plurality of projection images, not all of the plurality of projection images.

The tomographic image generating apparatus according the aspect of the present disclosure may further comprise a projection unit that projects the plurality of projection images on the corresponding tomographic plane based on a positional relationship between the radiation source position and the detection unit in a case of imaging the plurality of projection images to acquire a tomographic plane projection image corresponding to each of the plurality of projection images, in which the positional shift amount derivation unit derives, as the positional shift amount between the plurality of projection images, a positional shift amount between a plurality of the tomographic plane projection images based on the body movement of the subject with the feature point as a reference on the corresponding tomographic plane.

In the tomographic image generating apparatus according to the aspect of the present disclosure, the positional shift amount derivation unit may set a local region corresponding to the feature point in the plurality of tomographic plane projection images, and derive the positional shift amount based on the local region.

In the tomographic image generating apparatus according to the aspect of the present disclosure, the positional shift amount derivation unit may set a plurality of first local regions including the feature point in the plurality of tomographic plane projection images, set a second local region including the feature point in the tomographic image in which the feature point is detected, derive a positional shift amount of each of the plurality of first local regions with respect to the second local region as a temporary positional shift amount, and derive the positional shift amount based on a plurality of the temporary positional shift amounts.

In this case, the positional shift amount derivation unit may derive the temporary positional shift amount based on a peripheral region of the feature point in the second local region.

The "local region" is a region including the feature point in the tomographic image or the tomographic plane projection image, and can be a region having any size smaller than the tomographic image or the tomographic plane projection image.

The local region needs to be larger than the range of movement as the body movement. The body movement may be about 2 mm in a case of being large. Therefore, in a case of the tomographic image or the tomographic plane projection image in which the size of one pixel is 100 μm square, the local region need only be, for example, a region of 50×50 pixels or 100×100 pixels around the feature point.

The "peripheral region of the feature point in the local region" means a region including the feature point in the local region and being smaller than the local region.

In the tomographic image generating apparatus according to the aspect of the present disclosure, the reconstruction unit may reconstruct the plurality of projection images excluding a target projection image which corresponds to a target tomographic plane projection image of which the positional shift amount is to be derived, and generates the plurality of tomographic images as target tomographic images, and the positional shift amount derivation unit may derive the positional shift amount of the target tomographic plane projection image by using the target tomographic images.

In the tomographic image generating apparatus according to the aspect of the present disclosure, the feature point detecting unit may detect a plurality of the feature points from the plurality of tomographic images, the tomographic image generating apparatus may further comprise a focal plane discrimination unit that discriminates whether the corresponding tomographic plane corresponding to the tomographic image in which each of the plurality of feature points is detected is a focal plane, and the positional shift amount derivation unit may derive the positional shift amount on the corresponding tomographic plane which is discriminated to be the focal plane.

The tomographic image generating apparatus according to the aspect of the present disclosure may further comprise a combining unit that combines two or more tomographic images among the plurality of tomographic images to generate a composite two-dimensional image, in which the feature point detecting unit detects a two-dimensional feature point in the composite two-dimensional image, and detects the feature point corresponding to the two-dimensional feature point from the plurality of tomographic images.

In the tomographic image generating apparatus according to the aspect of the present disclosure, the reconstruction unit may reconstruct all or a part of the plurality of projection images while correcting the positional shift amount to generate a plurality of the corrected tomographic images on the plurality of tomographic planes of the subject as a plurality of new tomographic images, the feature point detecting unit may detect the feature point from the plurality of new tomographic images, the positional shift amount derivation unit may derive a new positional shift amount between the plurality of new projection images, and the reconstruction unit may reconstruct the plurality of projection images while correcting the new positional shift amount to generate a new corrected tomographic image on at least one tomographic plane of the subject.

In the tomographic image generating apparatus according to the aspect of the present disclosure, the reconstruction unit, the feature point detecting unit, and the positional shift amount derivation unit may repeat generating of the new tomographic image, detecting of the feature point from the new tomographic image, and deriving of the new positional shift amount until the new positional shift amount converges.

"Repeat until convergence" means to repeat until the positional shift amount between the plurality of new tomographic plane projection images is equal to or smaller than a predetermined threshold.

The tomographic image generating apparatus according to the aspect of the present disclosure may further comprise a positional shift amount determination unit that performs image quality evaluation for a region of interest including the feature point in the corrected tomographic image, and determines whether the derived positional shift amount is appropriate or inappropriate based on a result of the image quality evaluation.

In the tomographic image generating apparatus according to the aspect of the present disclosure, the positional shift amount determination unit may perform the image quality evaluation for the region of interest including the feature point in the tomographic image, compare the result of the image quality evaluation for the corrected tomographic image with a result of the image quality evaluation for the tomographic image, and decide the tomographic image with a better result of the image quality evaluation as a final tomographic image.

The tomographic image generating apparatus according to the aspect of the present disclosure may further comprise an evaluation function derivation unit that derives an evaluation function for performing image quality evaluation for a region of interest including the feature point in the corrected tomographic image, in which the positional shift amount derivation unit derives the positional shift amount for optimizing the evaluation function.

In the tomographic image generating apparatus according to the aspect of the present disclosure, the subject may be a breast.

In the tomographic image generating apparatus according the aspect of the present disclosure, the positional shift amount derivation unit may change a search range in a case of deriving the positional shift amount depending on at least one of a density of a mammary gland, a size of the breast, an imaging time of the tomosynthesis imaging, a compression pressure of the breast in a case of the tomosynthesis imaging, or an imaging direction of the breast.

A tomographic image generating method according to another aspect of the present disclosure comprises acquiring a plurality of projection images corresponding to a plurality of radiation source positions, the plurality of projection images being generated by causing an imaging apparatus to perform tomosynthesis imaging in which a radiation source is moved relative to a detection surface of a detection unit in order to emit radiation to a subject at the plurality of radiation source positions according to movement of the radiation source, reconstructing all or a part of the plurality of projection images to generate a tomographic image on each of a plurality of tomographic planes of the subject, detecting at least one feature point from a plurality of the tomographic images, deriving a positional shift amount between the plurality of projection images based on body movement of the subject with the feature point as a reference on a corresponding tomographic plane corresponding to the tomographic image in which the feature point is detected, and reconstructing the plurality of projection images by correcting the positional shift amount to generate a corrected tomographic image on at least one tomographic plane of the subject.

A program causing a computer to execute the tomographic image generating method according to the aspect of the present disclosure may be provided.

A tomographic image generating apparatus according to still another aspect of the present disclosure comprises a memory that stores a command to be executed by a computer, and a processor configured to execute the stored command, in which processor executes processing of acquiring a plurality of projection images corresponding to a plurality of radiation source positions, the plurality of projection images being generated by causing an imaging apparatus to perform tomosynthesis imaging in which a radiation source is moved relative to a detection surface of a detection unit in order to emit radiation to a subject at the plurality of radiation source positions according to movement of the radiation source, reconstructing all or a part of the plurality of projection images to generate a tomographic image on each of a plurality of tomographic planes of the subject, detecting at least one feature point from a plurality of the tomographic images, deriving a positional shift amount between the plurality of projection images based on body movement of the subject with the feature point as a reference on a corresponding tomographic plane corresponding to the tomographic image in which the feature point is detected, and reconstructing the plurality of projection images by correcting the positional shift amount to generate a corrected tomographic image on at least one tomographic plane of the subject.

According to the present disclosure, it possible to acquire a high-quality tomographic image in which the body movement is accurately corrected.

BRIEF DESCRIPTION OF THE DRAWINGS

FIG. 16 is a flowchart showing a process performed in the first embodiment.

FIG. 17 is a diagram showing an image in a region of interest in a case where no body movement occurs in a second embodiment.

DETAILED DESCRIPTION

Figure 1:
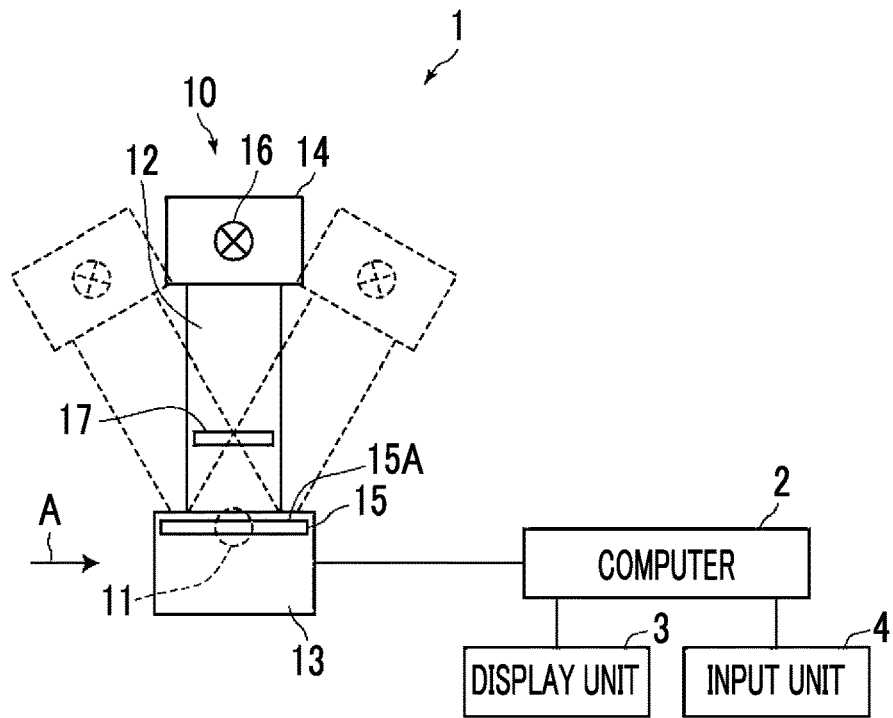
FIG. 1 is a schematic configuration diagram of a radiation image capturing apparatus to which a tomographic image generating apparatus according to a first embodiment of the present disclosure is applied.
Figure 2:
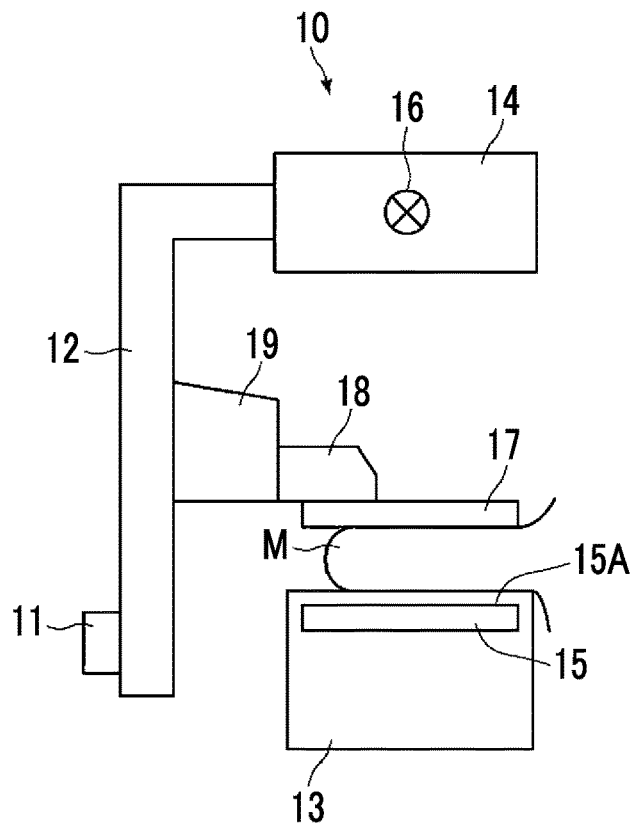
FIG. 2 is a diagram of the radiation image capturing apparatus as viewed from the direction of arrow A in FIG. 1.

Hereinafter, the embodiments of the present disclosure will be described with reference to the diagrams. FIG. 1 is a schematic configuration diagram of a radiation image capturing apparatus to which a tomographic image generating apparatus according to a first embodiment of the present disclosure is applied, and FIG. 2 is a diagram of the radiation image capturing apparatus as viewed from the direction of arrow A in FIG. 1. A radiation image capturing apparatus 1 is a mammography imaging apparatus that acquires a plurality of radiation images, that is, a plurality of projection images, by imaging a breast M, which is a subject, from a plurality of radiation source positions in order to generate a tomographic image by performing tomosynthesis imaging of the breast. As shown in FIG. 1, the radiation image capturing apparatus 1 comprises an imaging unit 10, a computer 2 connected to the imaging unit 10, and a display unit 3 and an input unit 4 which are connected to the computer 2.

The imaging unit 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the computer 2.

The imaging table 13 comprises a radiation detector 15 such as a flat panel detector therein. The radiation detector 15 has a detection surface 15A of radiation such as X-rays. In addition, a circuit board on which a charge amplifier for converting a charge signal read from the radiation detector 15 into a voltage signal, a correlated double sampling circuit for sampling the voltage signal output from the charge amplifier, an analog digital (AD) conversion unit for converting the voltage signal into a digital signal, and the like are provided is provided inside the imaging table 13. The radiation detector 15 corresponds to a detection unit. Although the radiation detector 15 is used as the detection unit in the present embodiment, the detection unit is not limited to the radiation detector 15 as long as radiation can be detected and converted into an image.

The radiation detector 15 can perform recording and reading of a radiation image repeatedly. A so-called direct-type radiation detector that directly converts radiation, such as X-rays, into electric charges may be used, or a so-called indirect-type radiation detector that converts radiation into visible light and then converts the visible light into a charge signal may be used. As a method of reading a radiation image signal, it is desirable to use a so-called thin film transistor (TFT) reading method in which a radiation image signal is read by ON and OFF of a TFT switch, or a so-called optical reading method in which a radiation image signal is read by emission of reading light. However, other methods may also be used without being limited to the above methods.

An X-ray source 16 that is a radiation source is housed inside the radiation emission unit 14. The timing of emission of X-ray that is radiation from the X-ray source 16, and an X-ray generation condition in the X-ray source 16, that is, selection of target and filter materials, a tube voltage, an emission time, and the like are controlled by the computer 2.

The arm unit 12 includes compression plate 17 disposed above the imaging table 13 to compress the breast M, a support unit 18 that supports the compression plate 17, and a moving mechanism 19 that moves the support unit 18 in the vertical direction in FIGS. 1 and 2. Information of the distance between the compression plate 17 and the imaging table 13, that is, a compression thickness is input to the computer 2.

The display unit 3 is a display device such as a cathode ray tube (CRT) or a liquid crystal monitor, and displays a message required for the operation, and the like in addition to a projection image, a two-dimensional image, and the generated tomographic image acquired as described later. The display unit 3 may include a speaker for outputting sound.

The input unit 4 includes an input device such as a keyboard, a mouse, or a touch panel system, and receives an operation of the radiation image capturing apparatus 1 by the operator. In addition, the input unit 4 receives an input of various kinds of information such as imaging conditions and the instruction of correction of the information, which are required to perform the tomosynthesis imaging. In the present embodiment, each part of the radiation image capturing apparatus 1 operates in accordance with the information input from the input unit 4 by the operator.

A tomographic image generating program according to the present embodiment is installed in the computer 2. In the present embodiment, the computer may be a workstation or a personal computer that is directly operated by the operator, or may be a server computer connected to these through a network. The tomographic image generating program is distributed in a state of being recorded on a recording medium such as a digital versatile disc (DVD) or a compact disc read only memory (CD-ROM), and is installed in the computer from the recording medium. Alternatively, the tomographic image generating program is stored in a storage device of a server computer connected to the network, or in a network storage so as to be accessible from the outside, and is downloaded and installed in the computer as necessary.

Figure 3:
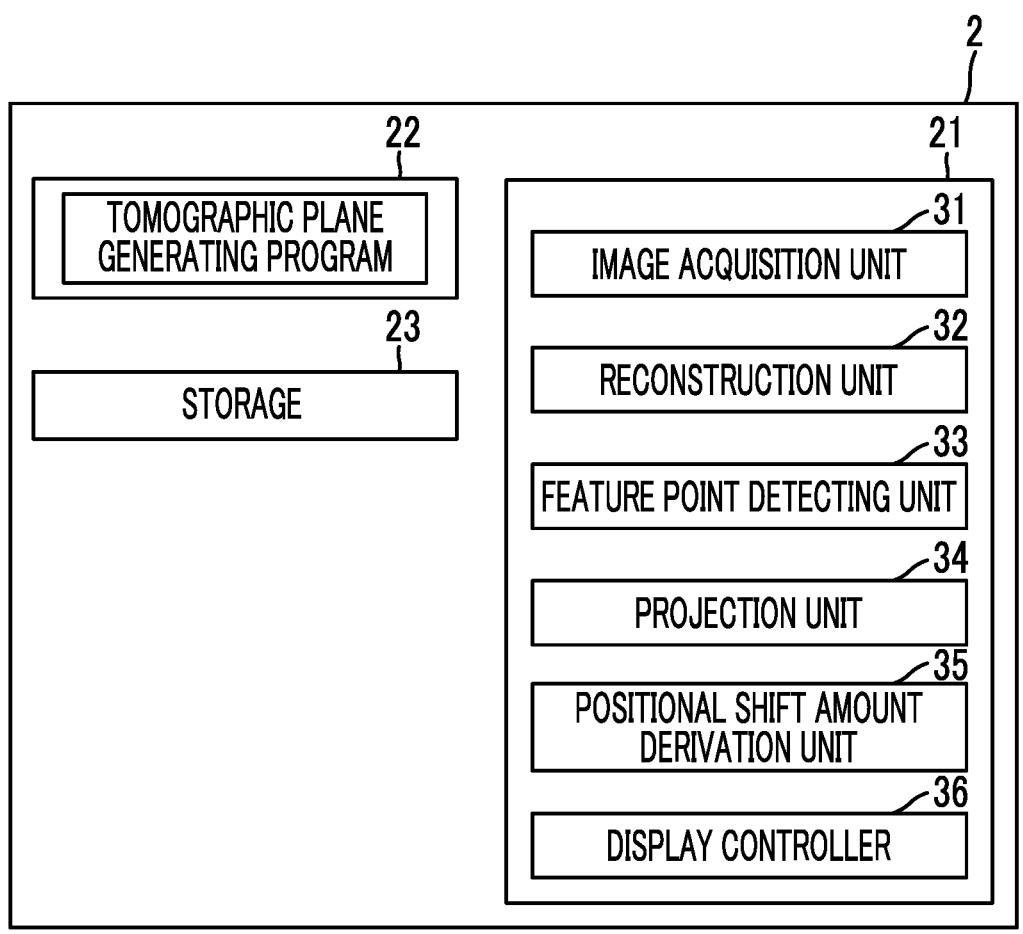
FIG. 3 is a diagram showing a schematic configuration of the tomographic image generating apparatus realized by installing a tomographic image generating program in a computer in the first embodiment.

FIG. 3 is a diagram showing a schematic configuration of the tomographic image generating apparatus realized by installing a tomographic image generating program in the computer 2 in the first embodiment. As shown in FIG. 3, the tomographic image generating apparatus comprises a central processing unit (CPU) 21, a memory 22, and a storage 23 as the configuration of a standard computer.

The storage 23 includes a storage device such as a hard disk drive or a solid state drive (SSD), and stores various kinds of information including a program for driving each unit of the radiation image capturing apparatus 1 and the tomographic image generating program. In addition, the storage 23 also stores the projection image acquired by tomosynthesis imaging, and the tomographic image and the tomographic plane projection image generated as described later.

The memory 22 temporarily stores programs and the like stored in the storage 23 so that the CPU 21 executes various kinds of processing. The tomographic image generating program defines, as the processing to be executed by the CPU 21, image acquisition processing of acquiring a plurality of projection images of the breast M corresponding to a plurality of radiation source positions by causing the radiation image capturing apparatus 1 to perform tomosynthesis imaging, reconstruction processing of reconstructing all or a part of the plurality of projection images to generate a tomographic image on each of a plurality of tomographic planes of the breast M which is the subject, feature point detecting processing of detecting at least one feature point from a plurality of the tomographic images, projection processing of projecting the plurality of projection images on the corresponding tomographic plane corresponding to the tomographic image in which the feature point is detected, based on a positional relationship between the position of the X-ray source 16 and the radiation detector 15 in a case of imaging the plurality of projection images, and acquiring a tomographic plane projection image corresponding to each of the plurality of projection images, positional shift amount derivation processing of deriving a positional shift amount between the plurality of tomographic plane projection images based on the body movement of the breast M with the feature point as a reference on a corresponding tomographic plane, reconstruction processing of reconstructing the plurality of projection images by correcting the positional shift amount to generate a corrected tomographic image on at least one tomographic plane of the subject, and display control processing of displaying the tomographic image and the like on the display unit 3.

Then, the CPU 21 executes these kinds of processing according to the tomographic image generating program, so that the computer 2 functions as an image acquisition unit 31, a reconstruction unit 32, a feature point detecting unit 33, a projection unit 34, a positional shift amount derivation unit 35, and a display controller 36.

In the case of performing image acquisition processing, the X-ray source 16 is moved by rotating the arm unit 12 around the rotary shaft 11, X-rays are emitted to the breast M as a subject at a plurality of radiation source positions according to the movement of the X-ray source 16 under the predetermined imaging conditions for tomosynthesis imaging, X-rays transmitted through the breast M are detected by the radiation detector 15, and a plurality of projection images Gi (i=1 to n, where n is the number of radiation source positions; for example, n=15) at a plurality of radiation source positions are acquired by the image acquisition unit 31.

Figure 4:
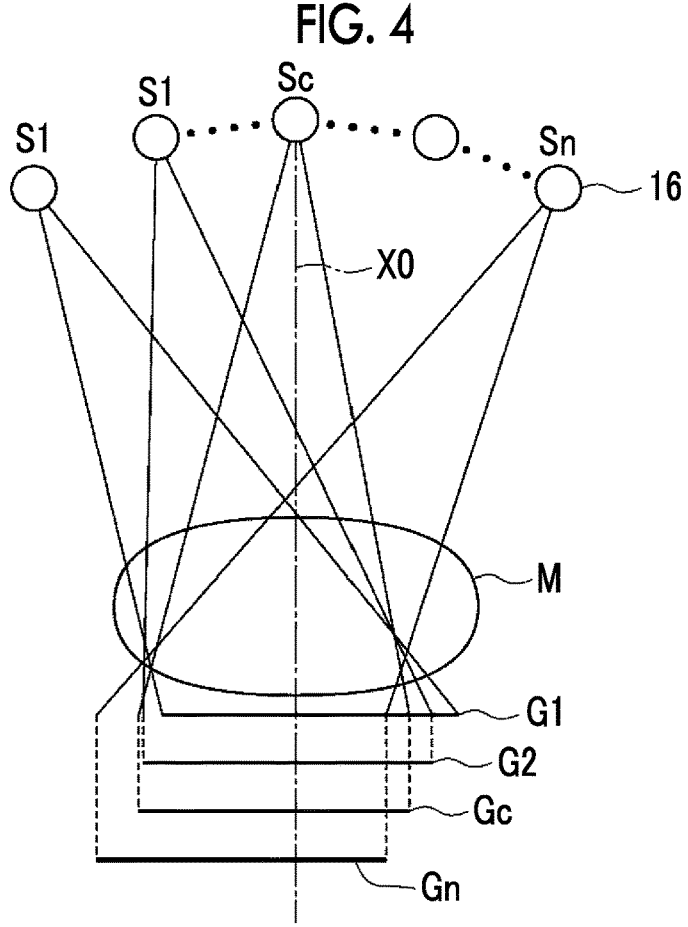
FIG. 4 is a diagram illustrating the acquisition of a projection image.

FIG. 4 is a diagram illustrating the acquisition of the projection image Gi. As shown in FIG. 4, the X-ray source 16 is moved to each radiation source position of S1, S2, . . . , Sn, the X-ray source 16 is driven at each radiation source position to irradiate the breast M with X-ray, and the X-rays transmitted through the breast M are detected by the radiation detector 15. As a result, the projection images G1, G2, . . . , Gn are acquired corresponding to the radiation source positions S1 to Sn. At each of the radiation source positions S1 to Sn, X-rays of the same dose are emitted to the breast M. The plurality of acquired projection images Gi are stored in the storage 23. The plurality of projection images Gi may be acquired by a program separate from the tomographic image generating program and stored in the storage 23 or the external storage device. In this case, the image acquisition unit 31 reads the plurality of projection images Gi stored in the storage 23 or the external storage device from the storage 23 or the external storage device for reconstruction processing and the like.

In FIG. 4, the radiation source position Sc is a radiation source position where an optical axis X0 of the X-rays emitted from the X-ray source 16 is perpendicular to the detection surface 15A of the radiation detector 15. The radiation source position Sc is referred to as a reference radiation source position Sc, and the projection image Gc acquired by irradiating the breast M with X-rays at the reference radiation source position Sc is referred to as a reference projection image Gc. Here, "the optical axis X0 of the X-ray is perpendicular to the detection surface 15A of the radiation detector 15" means that the optical axis X0 of the X-ray crosses the detection surface 15A of the radiation detector 15 at an angle of 90°. However, without being limited to this, a case where the optical axis X0 of the X-rays crosses the detection surface 15A of the radiation detector 15 with a certain degree of error with respect to 90° may be included. For example, a case where the optical axis X0 of the X-ray crosses the detection surface 15A of the radiation detector 15 with an error of about ±3° with respect to 90° is included in "the optical axis X0 of the X-ray is perpendicular to the detection surface 15A of the radiation detector 15" in the present embodiment.

Figure 5:
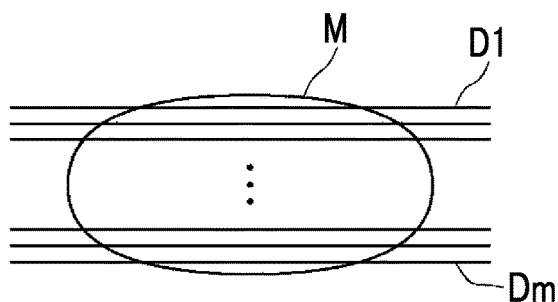
FIG. 5 is a diagram illustrating the generation of a tomographic image.

The reconstruction unit 32 reconstructs all or a part of the plurality of projection images Gi to generate the tomographic image in which a desired tomographic plane of the breast M is emphasized. Specifically, the reconstruction unit 32 reconstructs all or a part of the plurality of projection images Gi by a well-known back projection method such as a simple back projection method or a filtered back projection method to generate a plurality of tomographic images Dj (j=1 to m) on each of a plurality of tomographic planes of the breast M, as shown in FIG. 5. In this case, a three-dimensional coordinate position in a three-dimensional space including the breast M is set, pixel values of corresponding pixel positions of the plurality of projection images Gi are reconstructed for the set three-dimensional coordinate position, and the pixel value of the coordinate position is calculated. In a case where the positional shift amount based on body movement of the breast M in the tomosynthesis imaging is derived as described later, the reconstruction unit 32 corrects the positional shift amount and reconstructs the plurality of projection images Gi to generate a corrected tomographic image in which body movement is corrected.

The feature point detecting unit 33 detects at least one feature point from a plurality of the tomographic images Dj.

Figure 6:
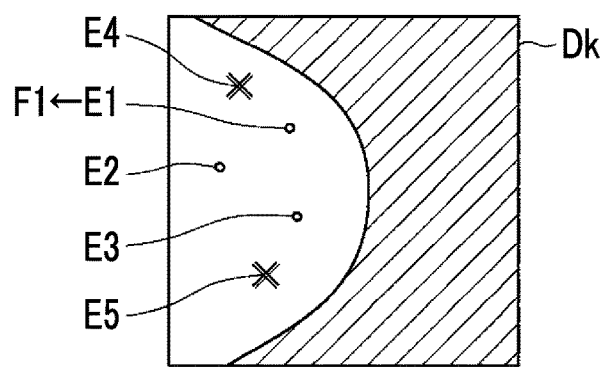
FIG. 6 is a diagram illustrating the detection of feature points from the tomographic image.

FIG. 6 is a diagram illustrating the detection of the feature points. Here, the detection of the feature points from one tomographic image Dk among the plurality of tomographic images Dj will be described. As shown in FIG. 6, the tomographic image Dk includes point-like structures E1 to E3 such as calcification, and intersections E4 and E5 of edges such as intersections of blood vessels on the tomographic plane of the breast M in which the tomographic image Dk is acquired.

The feature point detecting unit 33 detects the point-like structure, such as calcification, as a feature point from the tomographic image Dk by using an algorithm of known computer aided diagnosis (hereinafter, referred to as CAD). In addition, edges, intersections of edges, corners of edges, and the like included in the tomographic image Dk are detected as feature points by using an algorithm such as a Harris's corner detection method, a scale-invariant feature transform (SIFT), features from accelerated segment test (FAST), or speeded up robust features (SURF). For example, the feature point detecting unit 33 detects a point-like structure E1 included in the tomographic image Dk shown in FIG. 6 as a feature point F1.

Here, for the sake of explanation, only one feature point F1 is detected from one tomographic image Dk, but it is preferable to detect a plurality of feature points. For example, all of point-like structures E1 to E3 and intersections E4 and E5 included in the tomographic image Dk shown in FIG. 6 may be detected as the feature points. The feature point may be only one pixel in the tomographic image Dk, or may be a plurality of pixels indicating the positions of feature structures. Also, for the sake of explanation, the feature point is detected only from one tomographic image Dk, but it is assumed that a plurality of feature points are actually detected from each of the plurality of tomographic images.

The projection unit 34 projects the plurality of projection images Gi on the corresponding tomographic plane which is the tomographic plane corresponding to the tomographic image in which the feature point F1 is detected, based on the positional relationship between the radiation source position and the radiation detector 15 in a case of imaging the plurality of projection images Gi. As a result, the projection unit 34 acquires the tomographic plane projection image GTi corresponding to each of the plurality of projection images Gi. Hereinafter, the acquisition of the tomographic plane projection image GTi will be described. In the present embodiment, since the feature points are detected in each of the plurality of tomographic images Dj, the plurality of projection images Gi are projected on the plurality of tomographic planes Tj corresponding to plurality of tomographic images Dj to generate the tomographic plane projection image GTi.

Figure 7:
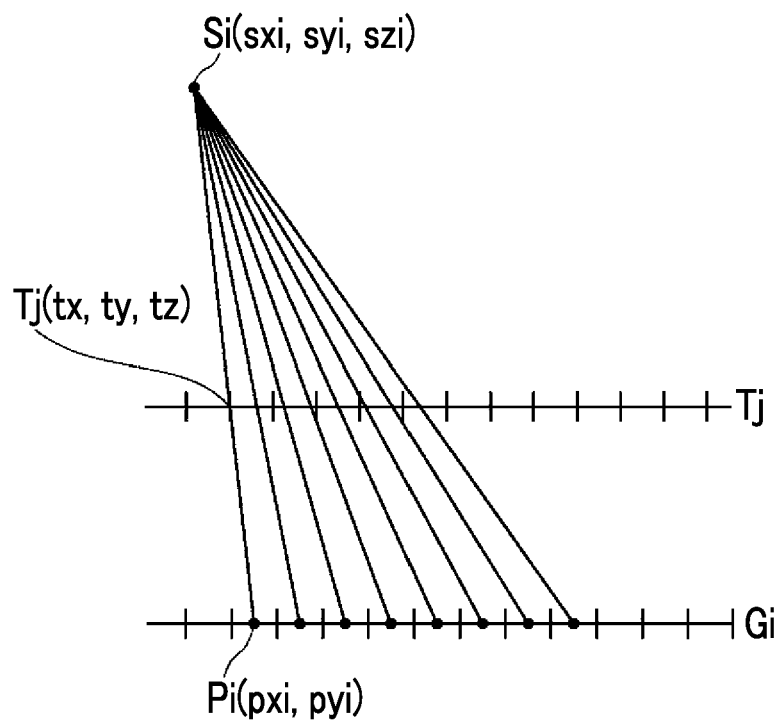
FIG. 7 is a diagram illustrating the generation of a tomographic plane projection image.

FIG. 7 is a diagram illustrating the projection of the projection image. In FIG. 7, a case will be described in which one projection image Gi acquired at the radiation source position Si is projected on one tomographic plane Tj of the breast M. In the present embodiment, as shown in FIG. 7, at the intersecting position of a straight line connecting the radiation source position Si and the pixel position on the projection image Gi, and the tomographic plane Tj, the pixel value of the projection image Gi positioned on the straight line is projected.

The tomographic image generated on the projection image Gi and the tomographic plane Tj is composed of a plurality of pixels discretely arranged two-dimensionally at a predetermined sampling interval, and pixels are arranged in grid points having a predetermined sampling interval. In FIG. 7, a short line segment orthogonal to the projection image Gi and the tomographic plane Tj indicates the pixel division position. Therefore, in FIG. 7, the center position of the pixel division position is the pixel position which is the grid point.

Here, the relationship of the coordinates $(sxi, syi, szi)$ of the radiation source position at the radiation source position Si, the coordinates $(pxi, pyi)$ of the pixel position Pi in the projection image Gi, and the coordinates $(tx, ty, tz)$ of the projection position on the tomographic plane Tj is expressed by Equation (1) below. In the present embodiment, a z-axis is set to a direction orthogonal to the detection surface 15A of the radiation detector 15, a y-axis is set to a direction parallel to a direction in which the X-ray source 16 moves in the detection surface of the radiation detector 15, and an x-axis is set to a direction orthogonal to the y-axis.

$$pxi=(tx \times szi - sxi \times tz)/(szi-tz)$$

$$pyi=(ty \times szi - syi \times tz)/(szi-tz) \quad (1)$$

Therefore, by setting pxi and pyi in Equation (1) to the pixel position of the projection image Gi, and solving Equation (1) for tx and ty, the projection position on the tomographic plane Tj on which the pixel value of the projection image Gi is projected can be calculated. Therefore, by projecting the pixel value of the projection image Gi on the projection position on the calculated tomographic plane Tj, the tomographic plane projection image GTi is generated.

Figure 8:
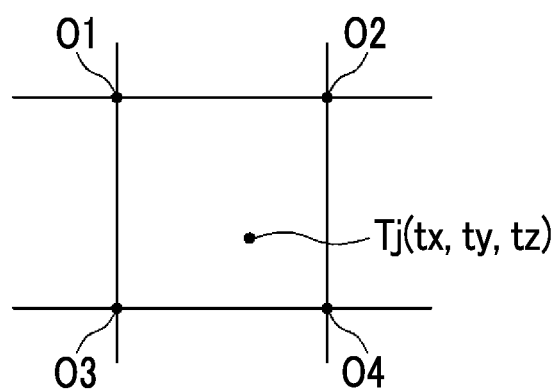
FIG. 8 is a diagram illustrating the interpolation of pixel values of the tomographic image.

In this case, the intersection point of the straight line connecting the radiation source position Si and the pixel position on the projection image Gi, and the tomographic plane Tj may not be positioned on the pixel position on the tomographic plane Tj. For example, as shown in FIG. 8, the projection position $(tx, ty, tz)$ on the tomographic plane Tj may be positioned between the pixel positions O1 to O4 of the tomographic image Dj on the tomographic plane Tj. In this case, the pixel value of each pixel position need only be calculated by performing an interpolation calculation using the pixel value of the projection image at the plurality of projection positions around the pixel positions O1 to O4. As the interpolation calculation, a linear interpolation calculation that weights the pixel value of the projection image at the projection position according to the distance between the pixel position and the plurality of projection positions around the pixel position can be used. In addition, any method such as a non-linear bicubic interpolation calculation using more pixel values of projection positions around the pixel position and a B-spline interpolation calculation can be used. Also, in addition to the interpolation calculation, the pixel value at the projection position closest to the pixel position may be used as the pixel value at the pixel position. As a result, for the projection image Gi, the pixel values at all of the pixel positions of the tomographic plane Tj can be obtained. In the present embodiment, for each of the plurality of projection images Gi, the tomographic plane projection image GTi having pixel values obtained at all of the pixel positions of the tomographic plane Tj is generated. Therefore, in one tomographic plane, the number of tomographic plane projection images GTi matches the number of projection images Gi.

Figure 9:
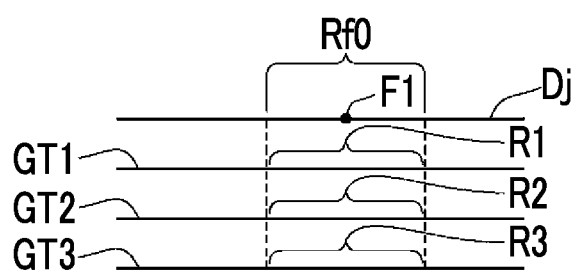
FIG. 9 is a diagram illustrating the setting of a region of interest.
Figure 10:
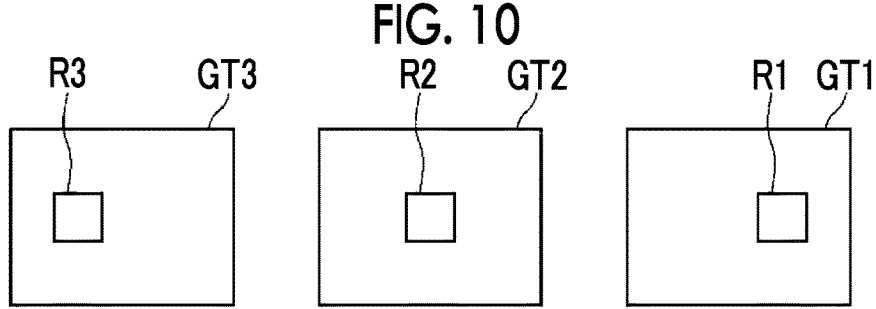
FIG. 10 is a diagram showing the region of interest set in the tomographic plane projection image.

The positional shift amount derivation unit 35 derives the positional shift amount between the plurality of tomographic plane projection images GTi based on the body movement of the breast M during the tomosynthesis imaging. First, the positional shift amount derivation unit 35 sets the local region corresponding to the feature point F1 as a region of interest for the plurality of tomographic plane projection images GTi. Specifically, the local region having a predetermined size centered on the coordinate position of the feature point F1 is set as the region of interest. FIG. 9 is a diagram illustrating the setting of a region of interest. In FIG. 9, for the sake of explanation, it is assumed that three projection images G1 to G3 are projected on the tomographic plane Tj to generate the tomographic plane projection images GT1 to GT3. As shown in FIG. 9, the positional shift amount derivation unit 35 sets the region of interest Rf0 centered on the coordinate position of the feature point F1 in the tomographic image Dj on the tomographic plane Tj. The regions of interest R1 to R3 corresponding to the region of interest Rf0 are set in the tomographic plane projection images GT1 to GT3. The broken line in FIG. 9 indicates the boundary between the regions of interest R1 to R3 and the other regions. Therefore, the positions of the region of interest Rf0 and the regions of interest R1 to R3 coincide with each other on the tomographic plane Tj. FIG. 10 is a diagram showing the regions of interest R1 to R3 set in the tomographic plane projection images GT1 to GT3. The body movement may be about 2 mm in a case of being large. Therefore, in a case of the tomographic image or the tomographic plane projection image in which the size of one pixel is 100 µm square, the regions of interest R1 to R3 need only be, for example, a region of 50×50 pixels or 100×100 pixels around the feature point F1.

Further, the positional shift amount derivation unit 35 performs registration of the regions of interest R1 to R3. At this time, the registration is performed with reference to the region of interest set in the reference tomographic plane projection image. In the present embodiment, the registration of other regions of interest is performed with reference to the region of interest set in the tomographic plane projection image (reference tomographic plane projection image) for reference projection image (referred to as Gs) acquired at the radiation source position Sc in which the optical axis X0 of the X-rays from the X-ray source 16 is orthogonal to the radiation detector 15.

Here, it is assumed that the region of interest R2 shown in FIG. 10 is set in the reference tomographic plane projection image. In this case, the positional shift amount derivation unit 35 performs the registration of the regions of interest R1 and R3 with respect to the region of interest R2, and derives the shift vector representing the movement direction and the movement amount of the regions of interest R1 and R3 with respect to the region of interest R2 as the positional shift amount. The registration means that the movement direction and the movement amount of the regions of interest R1 and R3 with respect to the region of interest R2 are obtained in a predetermined search range such that the correlation between the regions of interest R1 and R3, and the region of interest R2. Here, the normalized cross correlation may be used as the correlation. Further, since the reference tomographic plane projection image of one of the tomographic plane projection images GTi is used as a reference, the shift vector is one less than the number of tomographic plane projection images. For example, in a case where the number of tomographic plane projection images is 15, the number of shift vectors is 14. In a case where the number of tomographic plane projection images is 3, the number of shift vectors is 2.

Figure 11:
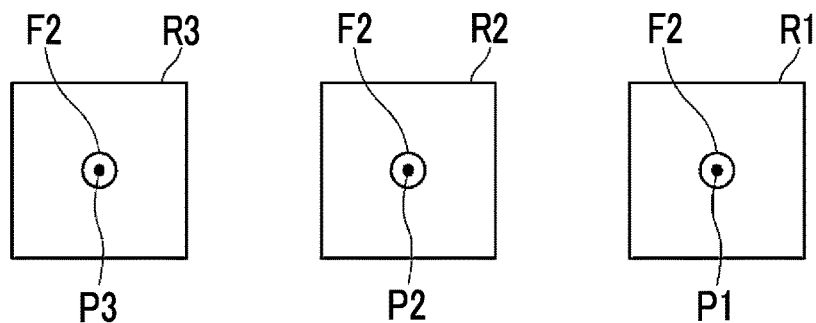
FIG. 11 is a diagram showing an image in the region of interest in a case where no body movement occurs in the first embodiment.

FIG. 11 is a diagram showing the image of three regions of interest R1 to R3 in a case where no body movement occurs during acquisition of the projection images G1 to G3. In FIG. 11, the center position of the regions of interest R1 to R3, that is, the positions P1 to P3 corresponding to the feature points F1 in the tomographic plane projection images GT1 to GT3 are shown, and images F2 of the feature points F1 included in the regions of interest R1 to R3 are indicated by a large circle. As shown in FIG. 11, in a case where no body movement occurs during the acquisition of the projection images G1 to G3, in all of three regions of interest R1 to R3, the positions P1 to P3 corresponding to the feature points F1 and the positions of the images F2 of the feature point s F1 match each other. Therefore, the shift vectors of the regions of interest R1 and R3 with respect to the region of interest R2, that is, the positional shift amounts are all 0.

Figure 12:
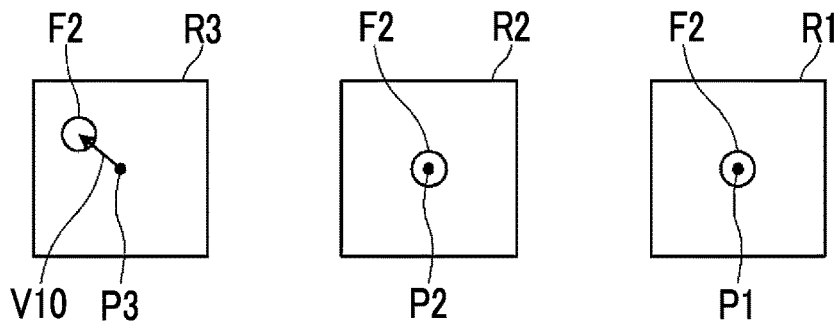
FIG. 12 is a diagram showing an image in the region of interest in a case where body movement occurs in the first embodiment.

FIG. 12 is a diagram showing the image of three regions of interest R1 to R3 in a case where body movement occurs during acquisition of the projection images G2 and G3 among the projection images G1 to G3. In FIG. 12, since no body movement occurs during the acquisition of the projection image G1 and the projection image G2, the positions P1 and P2 corresponding to the feature point F1 in the regions of interest R1 and R2 and the position of the image F2 of the feature point F1 included in the regions of interest R1 and R2 match each other. For this reason, the positional shift amount of the region of interest R1 with respect to the region of interest R2 is 0. On the other hand, since no body movement occurs during the acquisition of the projection image G2 and the projection image G3, the position P3 corresponding to the feature point F1 in the region of interest R3 and the position of the image F2 of the feature point F1 included in the region of interest R3 match each other. Therefore, due to the movement amount and the movement direction of the region of interest R3 with respect to the region of interest R2, the shift vector V10 having a size and a direction is derived as the positional shift amount.

Figure 13:
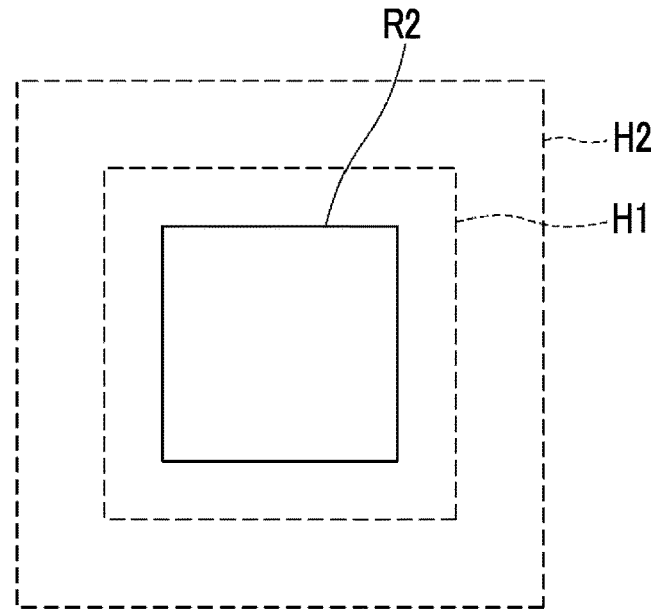
FIG. 13 is a diagram illustrating a search range of the region of interest.

In a case where the positional shift amount is derived, a search range in a case of deriving the positional shift amount may be changed depending on at least one of a density of a mammary gland for the breast M, a size of the breast M, an imaging time of the tomosynthesis imaging, a compression pressure of the breast M in a case of the tomosynthesis imaging, or an imaging direction of the breast. FIG. 13 is a diagram illustrating the change of the search range. As shown in FIG. 13, two types of search ranges, a small search range H1 and a large search range H2, are set as the search ranges of the regions of interest R1 and R3 with respect to the region of interest R2 which is a reference.

Here, in a case where the density of the mammary gland is small, the amount of fat in the breast M is large, and thus the body movement tends to be large in a case of imaging. Also, in a case where the breast M is large, the body movement tends to be large in a case of imaging. In addition, as the tomosynthesis imaging time is longer, the body movement during imaging tends to be large. Further, in a case where the imaging direction of the breast M is a medio-lateral oblique (MLO) direction, the body movement in a case of imaging tends to be large than a cranio-caudal (CC) direction.

Therefore, it is preferable that the positional shift amount derivation unit 35 changes a search range in a case of deriving the positional shift amount by receiving, from the input unit 4, the input of at least one information of a density of a mammary gland for the breast M, a size of the breast M, an imaging time of the tomosynthesis imaging, a compression pressure of the breast M in a case of the tomosynthesis imaging, or an imaging direction of the breast M. Specifically, in a case where the body movement tends to increase, the large search range H2 shown in FIG. 13 need only be set.

On the contrary, in a case where the body movement tends to increase, the small search range H1 shown in FIG. 13 need only be set.

Figure 14:
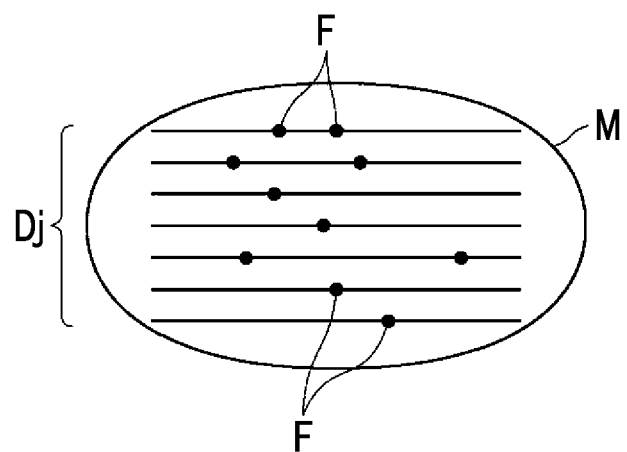
FIG. 14 is a diagram showing the feature points in a three-dimensional space.

In the above, for the sake of explanation, the positional shift amount between the plurality of tomographic plane projection image GTi is derived for one feature point F1 is detected on one tomographic plane Tj. In practice, however, as shown in FIG. 14, the positional shift amount derivation unit 35 derives a positional shift amount for a plurality of different feature points F (here, ten feature points shown by black circles) in a three-dimensional space in the breast M expressed by the plurality of tomographic images Dj. As a result, for the tomographic plane projection image corresponding to the projection image acquired in a state in which body movement occurs, positional shift amounts for a plurality of different feature points F are derived. The positional shift amount derivation unit 35 interpolates the positional shift amounts for the plurality of different feature points F with respect to the coordinate positions of the three-dimensional space for generating the tomographic image Dj. As a result, for the tomographic plane projection image acquired in a state in which body movement occurs, the positional shift amount derivation unit 35 derives the positional shift amounts in a case of performing reconstruction for all of the coordinate positions of the three-dimensional space for generating a tomographic image.

The reconstruction unit 32 reconstructs the projection image Gi while correcting the derived positional shift amount to generate the corrected tomographic image Dhj in which the body movement is corrected. Specifically, in a case where the back projection method is used for reconstruction, the pixel of the projection image Gi in which the positional shift occurs is reconstructed by correcting the positional shift such that the pixel corresponding to the other projection image is projected on the position to be back projected, based on the derived positional shift amount.

Instead of deriving the positional shift amount at the plurality of different feature points F, one positional shift amount may be derived from the plurality of different feature points F. In this case, the region of interest is set for each of the plurality of different feature points F, and the positional shift amount is derived on the assumption that the entire region of interest moves in the same direction by the same amount. In this case, the positional shift amount need only be derived such that the representative values (for example, mean value, median value, or maximum value) of the correlation for all of the regions of interest between the tomographic plane projection images that are target of positional shift amount derivation are maximized. Here, in a case where the signal-to-noise ratio of each feature point F in the tomographic plane projection image is not very good, the accuracy of deriving the positional shift amount deteriorates. However, by deriving one positional shift amount from the plurality of different feature points F in this way, even in a case where the signal-to-noise ratio of each feature point F is not very good, the accuracy of deriving the positional shift amount can be improved.

The three-dimensional space in the breast M represented by the plurality of tomographic images Dj may be divided into a plurality of three-dimensional regions, and one positional shift amount may be derived from the plurality of feature points F in the same manner as described above for each region.

Figure 15:
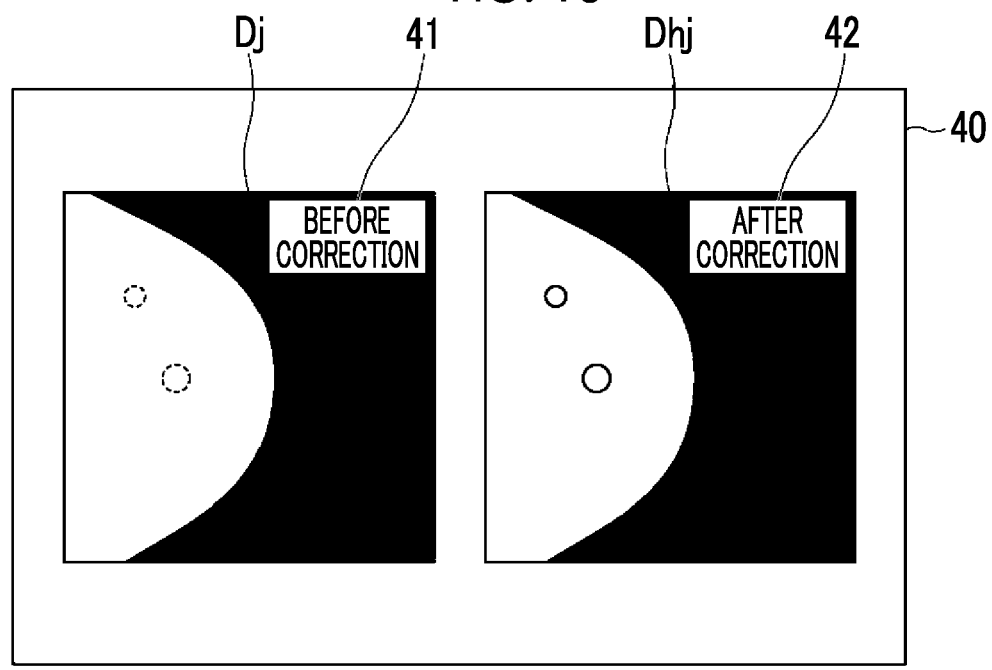
FIG. 15 is a diagram showing a display screen for a corrected tomographic image.

The display controller 36 displays the generated corrected tomographic image on the display unit 3. FIG. 15 is a diagram showing the display screen of the corrected tomographic image. As shown in FIG. 15, the tomographic image Dj before body movement correction and the corrected tomographic image Dhj subjected to body movement correction are displayed on a display screen 40. A label 41 of "before correction" is given to the tomographic image Dj so that it can be seen that the body movement is not corrected. A label 42 of "after correction" is given to the corrected tomographic image Dhj such that it can be seen that body movement is corrected. The label 41 may be given only to the tomographic image Dj, or the label 42 may be given only to the corrected tomographic image Dhj. It is needless to say that only the corrected tomographic image Dhj may be displayed. In FIG. 15, a broken line indicates that the structures included in the tomographic image Dj before correction is blurred, and a solid line indicates that the structures included in the corrected tomographic image Dhj is not blurred.

Further, it is preferable that the tomographic image Dj and the corrected tomographic image Dhj display the same cross section. In a case of switching the tomographic plane to be displayed according to the instruction from the input unit 4, it is preferable to link the tomographic plane to be displayed in the tomographic image Dj and the corrected tomographic image Dhj. In addition to the tomographic image Dj and the corrected tomographic image Dhj, the projection image Gi may be displayed.

The operator can confirm the success or failure of the body movement correction by looking at the display screen 40. Further, in a case where the body movement is too large, even in a case where the tomographic image is generated by performing reconstruction while correcting the positional shift amount as in the present embodiment, the body movement cannot be corrected accurately, and the body movement correction may fail. In such a case, the tomographic image Dj may have a higher image quality than the corrected tomographic image Dhj due to the failure of the body movement correction. Therefore, the input unit 4 may receive an instruction to store any of the tomographic image Dj or the corrected tomographic image Dhj, and the instructed image may be stored in the storage 23 or the external storage device.

Next, the processing performed in the first embodiment will be described. FIG. 16 is a flowchart showing a process performed in the first embodiment. In a case where the instruction of an operator to start the processing is received through the input unit 4, the image acquisition unit 31 causes the radiation image capturing apparatus 1 to perform the tomosynthesis imaging to acquire a plurality of projection images Gi (step ST1). Then, the reconstruction unit 32 reconstructs all or a part of the plurality of projection images Gi to generate a plurality of tomographic images Dj (step ST2). Then, the feature point detecting unit 33 detects at least one feature point from a plurality of the tomographic images Dj (step ST3). The projection unit 34 projects the plurality of projection images Gi on the corresponding tomographic plane corresponding to the tomographic image in which the feature point F1 is detected, based on the positional relationship between the radiation source position and the radiation detector 15 in a case of imaging the plurality of projection images Gi, and acquires the tomographic plane projection image GTi corresponding to each of the plurality of projection images Gi (step ST4).

Next, the positional shift amount derivation unit 35 derives the positional shift amount between the plurality of tomographic plane projection image GTi (step ST5). Further, the reconstruction unit 32 reconstructs the plurality of projection images Gi while correcting the positional shift amount, and thereby generates a corrected tomographic image Dhj (step ST6). Then, the display controller 36 displays the corrected tomographic image Dhj on the display unit 3 (step ST7), and the processing is terminated. The generated corrected tomographic image Dhj is transmitted to the external storage device (not shown) and stored.

As described above, according to the first embodiment, the plurality of projection images Gi by tomosynthesis imaging are acquired, all or a part of the plurality of projection images Gi are reconstructed, and the tomographic image Dj of each of the plurality of tomographic plane Tj of the breast M are generated. At least one feature point is detected from the plurality of tomographic images Dj, the plurality of projection images Gi are projected on the corresponding tomographic plane corresponding to the tomographic image in which the feature point is detected, based on the positional relationship between the radiation source position and the radiation detector 15 in a case of imaging the plurality of projection images Gi, and the tomographic plane projection image GTi corresponding to each of the plurality of projection images Gi are acquired. Further, on the corresponding tomographic plane, the positional shift amount between the plurality of tomographic plane projection images is derived with the feature point as a reference, and the plurality of projection images Gi are reconstructed by correcting the positional shift amount to generate the corrected tomographic image Dhj.

As described above, in the first embodiment, the feature points are detected from the plurality of tomographic images Dj, not from the projection image Gi or the tomographic plane projection image GTi. Here, the tomographic image Dj includes only the structures included on the corresponding tomographic plane Tj. Therefore, the structures on other tomographic planes included in the projection image Gi are not included in the tomographic image Dj. Therefore, according to the first embodiment, the feature points can be detected accurately without being affected by the structures of other tomographic planes. Therefore, the positional shift amount between the plurality of projection images Gi can be appropriately derived, and as a result, according to the present embodiment, a high-quality corrected tomographic image Dhj with reduced effects of body movement can be acquired.

Hereinafter, the second embodiment of the present disclosure will be described. The configuration of the tomographic image generating apparatus according to the second embodiment is the same as the configuration of the tomographic image generating apparatus according to the first embodiment shown in FIG. 3, only the processing to be performed is different, and thus the detailed description of the apparatus is omitted. In the first embodiment, the positional shift amount is derived between the tomographic plane projection images GTi. In the second embodiment, the region of interest Rf0 centered on the coordinate position of the feature point F1 is set in the tomographic image Dj, and the positional shift amount of the region of interest Ri set in the tomographic plane projection image GTi with respect to the set region of interest Rf0 is derived as a temporary positional shift amount. Then, the difference from the first embodiment is that the positional shift amount between the plurality of tomographic plane projection images GTi is derived based on the derived amount of temporary positional shift amount. The region of interest Ri set in the plurality of tomographic plane projection images GTi corresponds to the first local region, and the region of interest Rf0 set in the tomographic image Dj corresponds to the second local region.

FIG. 17 is a diagram illustrating the derivation of the positional shift amount in the second embodiment. The region of interest Rf0 and the regions of interest R1 to R3 in FIG. 17 are the same as the region of interest Rf0 and the regions of interest R1 to R3 shown in FIG. 9. In the second embodiment, first, the positional shift amount derivation unit 35, as reference to the region of interest Rf0 set in the tomographic image Dj, derives the positional shift amounts of the regions of interest R1 to R3 set in the tomographic plane projection image GTi (GT1 to GT3 in FIG. 17) with respect to the region of interest Rf0 as a temporary positional shift amount. In a case where no body movement occurs during the acquisition of the projection images G1 to G3, in all of three regions of interest R1 to R3, the positions P1 to P3 corresponding to the feature points F1 and the positions of the images F2 of the feature point s F1 match each other. Therefore, the shift vectors (hereinafter, referred to as Vf1, Vf2, and Vf3) of the regions of interest R1 to R3 with respect to the region of interest Rf0, that is, the temporary positional shift amounts are all 0.

Figure 18:
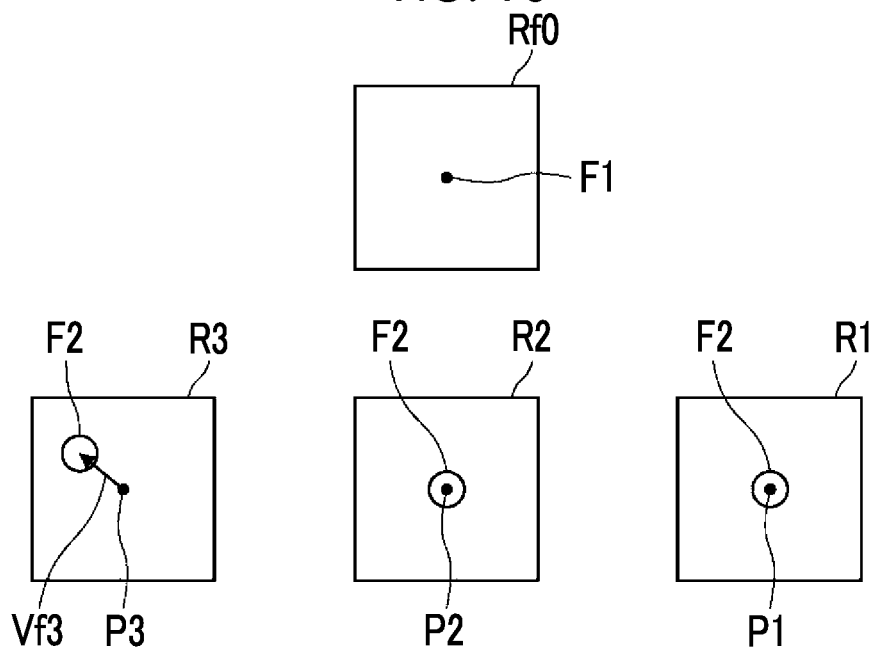
FIG. 18 is a diagram showing an image in the region of interest in a case where body movement occurs in the second embodiment.

FIG. 18 is a diagram showing the image of three regions of interest R1 to R3 in a case where body movement occurs during acquisition of the projection images G2 and G3 among the projection images G1 to G3. In FIG. 18, since no body movement occurs during the acquisition of the projection image G1 and the projection image G2, the positions P1 and P2 corresponding to the feature point F1 in the regions of interest R1 and R2 and the position of the image F2 of the feature point F1 included in the regions of interest R1 and R2 match each other. For this reason, the positional shift amount of the region of interest R1 and R2 with respect to the region of interest Rf0 is 0. On the other hand, since no body movement occurs during the acquisition of the projection image G2 and the projection image G3, the position P3 corresponding to the feature point F1 in the region of interest R3 and the position of the image F2 of the feature point F1 included in the region of interest R3 match each other. Therefore, the movement amount and the movement direction of the region of interest R3 are generated with respect to the region of interest Rf0. Therefore, the shift vectors Vf1 and Vf2 of the regions of interest R1 and R2 with respect to the region of interest Rf0, that is, the temporary positional shift amount is 0, but the shift vector Vf3 of the region of interest R3 with respect to the region of interest Rf0, that is, the temporary positional shift amount has a value.

In the second embodiment, the positional shift amount derivation unit 35 derives the positional shift amount between the tomographic plane projection images GTi based on the temporary positional shift amount. Specifically, as in the first embodiment, the positional shift amount is derived with reference to the projection image acquired at the reference radiation source position Sc in which the optical axis X0 of the X-rays from the X-ray source 16 is orthogonal to the radiation detector 15. Here, in a case where the projection image G2 is a reference tomographic plane projection image, the positional shift amount derivation unit 35 derives the positional shift amounts of the tomographic plane projection image GT1 and the tomographic plane projection image GT2 by the difference value Vf1−Vf2 of the shift vectors Vf1 and Vf2 of the regions of interest R1 and R2 with respect to the region of interest Rf0. Also, the positional shift amount derivation unit 35 derives the positional shift amounts of the tomographic plane projection image GT3 and the tomographic plane projection image GT2 by the difference value Vf3−Vf2 of the shift vectors Vf3 and Vf2 of the regions of interest R3 and R2 with respect to the region of interest Rf0.

As described above, in the second embodiment, the temporary positional shift amounts of the regions of interest R1 to R3 set on the tomographic plane projection image GTi with respect to the region of interest Rf0 set on the tomographic image Dj are derived, and the positional shift amount between the tomographic plane projection image GTi is derived based on the temporary positional shift amount. Here, since the region of interest Rf0 is set on the tomographic image Dj, unlike the projection image Gi, only the structures on the tomographic plane from which the tomographic image Dj is acquired are included. Therefore, according to the second embodiment, the positional shift amount is derived by reducing the influence of the structures included on the tomographic plane other than the tomographic plane in which the feature points are set. Therefore, according to the second embodiment, the influence of the structures on other tomographic planes can be reduced, the positional shift amount between the plurality of projection images Gi can be accurately derived, and as a result, according to the second embodiment, a high-quality corrected tomographic image Dhj with reduced effects of body movement can be acquired.

In the second embodiment, as in the first embodiment, a search range in a case of deriving the positional shift amount may be changed depending on at least one of a density of a mammary gland for the breast M, a size of the breast M, an imaging time of the tomosynthesis imaging, a compression pressure of the breast M in a case of the tomosynthesis imaging, or an imaging direction of the breast M.

Figure 19:
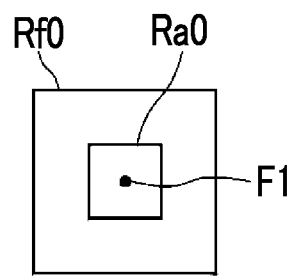
FIG. 19 is a diagram illustrating a peripheral region of the feature point.

Further, in the second embodiment, the shift vectors Vf1 to Vf3 of the regions of interest R1 to R3 with respect to the region of interest Rf0 are derived as a temporary positional shift amount, but in this case, the peripheral region Ra0 that is smaller than the region of interest Rf0 may be set around the feature point F1 of the region of interest Rf0 as shown in FIG. 19, and the shift vector may be derived based on the peripheral region Ra0. In this case, the shift vector may be derived using only the peripheral region Ra0. Further, in a case of deriving the correlation between the regions of interest R1 to R3, the peripheral region Ra0 may be weighted larger than the regions other than the peripheral region Ra0 in the regions of interest R1 to R3.

Further, in the second embodiment, the region of interest Rf0 is set in the tomographic image Dj, but the tomographic image to be generated may be different for each tomographic plane projection image GTi from which the temporary positional shift amount is derived. Specifically, it is preferable to generate the tomographic image excluding the target projection image corresponding to the target tomographic plane projection image to be derived from which the temporary positional shift amount is derived. Hereinafter, this case will be described as the third embodiment.

Figure 20:
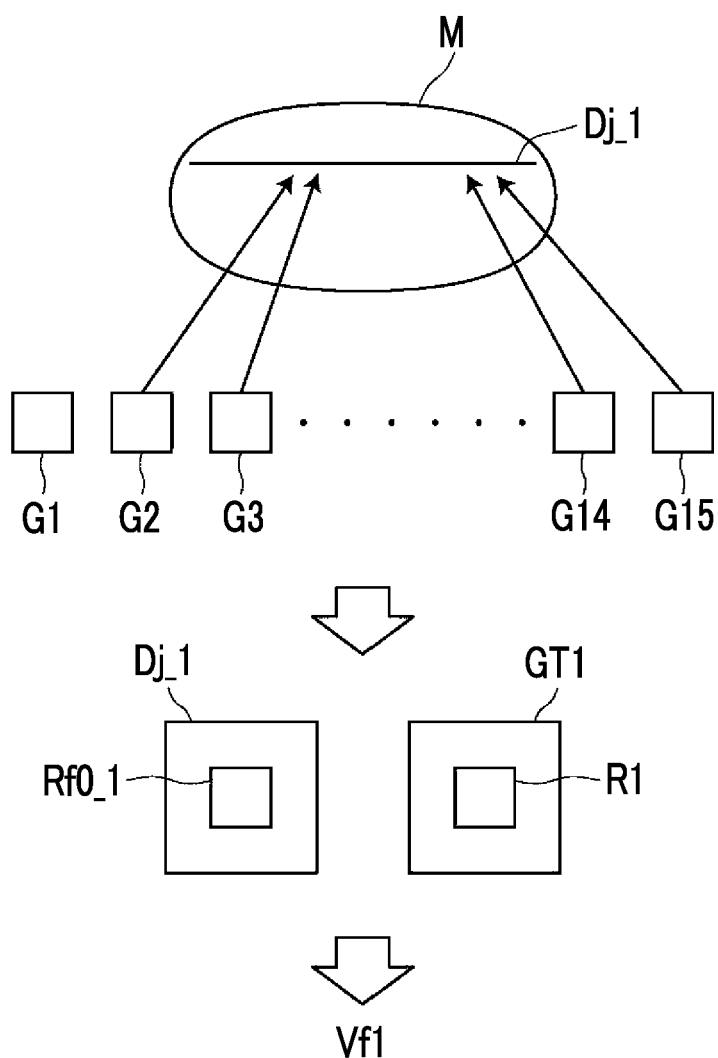
FIG. 20 is a diagram schematically showing a process performed in a third embodiment.

FIG. 20 is a diagram schematically showing a process performed in a third embodiment. Here, a case will be described in which on the tomographic plane Tj of the breast M, the temporary positional shift amount for the projection image G1 is derived with the projection image G1 as the target projection image among fifteen projection images G1 to G15, and the tomographic plane projection image GT1 as the target tomographic plane projection image. In this case, the reconstruction unit 32 reconstructs the projection images G2 to G15 excluding the projection image G1 on the tomographic plane Tj to generate a tomographic image (referred to as Dj_1). Then, the feature point detecting unit 33 detects the feature point from the tomographic image Dj_1, the projection unit 34 generates the tomographic plane projection images GT1 to GT15 from the projection images G1 to G15, and the positional shift amount derivation unit 35 sets the region of interest Rf0_1 on the tomographic image Dj_1, and derives the shift vector Vf1 of the region of interest R1 set on the tomographic plane projection image GT1 with respect to the region of interest Rf0_1 as the temporary positional shift amount.

In a case of deriving the temporary positional shift amount for the projection image G2, the reconstruction unit 32 reconstructs the projection images G1, G3 to G15 excluding the projection image G2 to generate the tomographic image (referred to as Dj_2). Then, the feature point detecting unit 33 detects the feature point from the tomographic image Dj_2, the projection unit 34 generates the tomographic plane projection images GT1 to GT15 from the projection images G1 to G15, and the positional shift amount derivation unit 35 sets the region of interest Rf0_2 on the tomographic image Dj_2, and derives the shift vector Vf2 of the region of interest R2 set on the tomographic plane projection image GT2 with respect to the region of interest Rf0_2 as the temporary positional shift amount.

Then, the target tomographic plane projection image is sequentially changed to derive the temporary positional shift amount for all of the tomographic plane projection images GTi, and as in the second embodiment, the positional shift amount between the tomographic plane projection images GTi is derived based on the temporary positional shift amount.

As described above, according to the third embodiment, the temporary positional shift amount is derived using the tomographic image that is not affected by the target projection image. Accordingly, the temporary positional shift amount can be more accurately derived, and as a result, the positional shift amount can be accurately derived.

In the third embodiment, the reconstructing of the tomographic image excluding the target projection image may be calculated, as shown in Equation (2) below, by subtracting the corresponding pixel value Gp of the target projection image from the pixel value Dp of each pixel of the tomographic image Dj generated by reconstructing all of the projection image Gi, and multiplying the subtracted pixel value by $n/(n-1)$. Although the method of Equation (2) is a simple method, the amount of calculation for generating the tomographic image excluding the target projection image can be reduced, and the processing for deriving the temporary positional shift amount can be performed at high speed.

$$\text{Tomographic image excluding target projection image} = (Dp - Gp) \times n/(n-1) \qquad (2)$$

Figure 21:
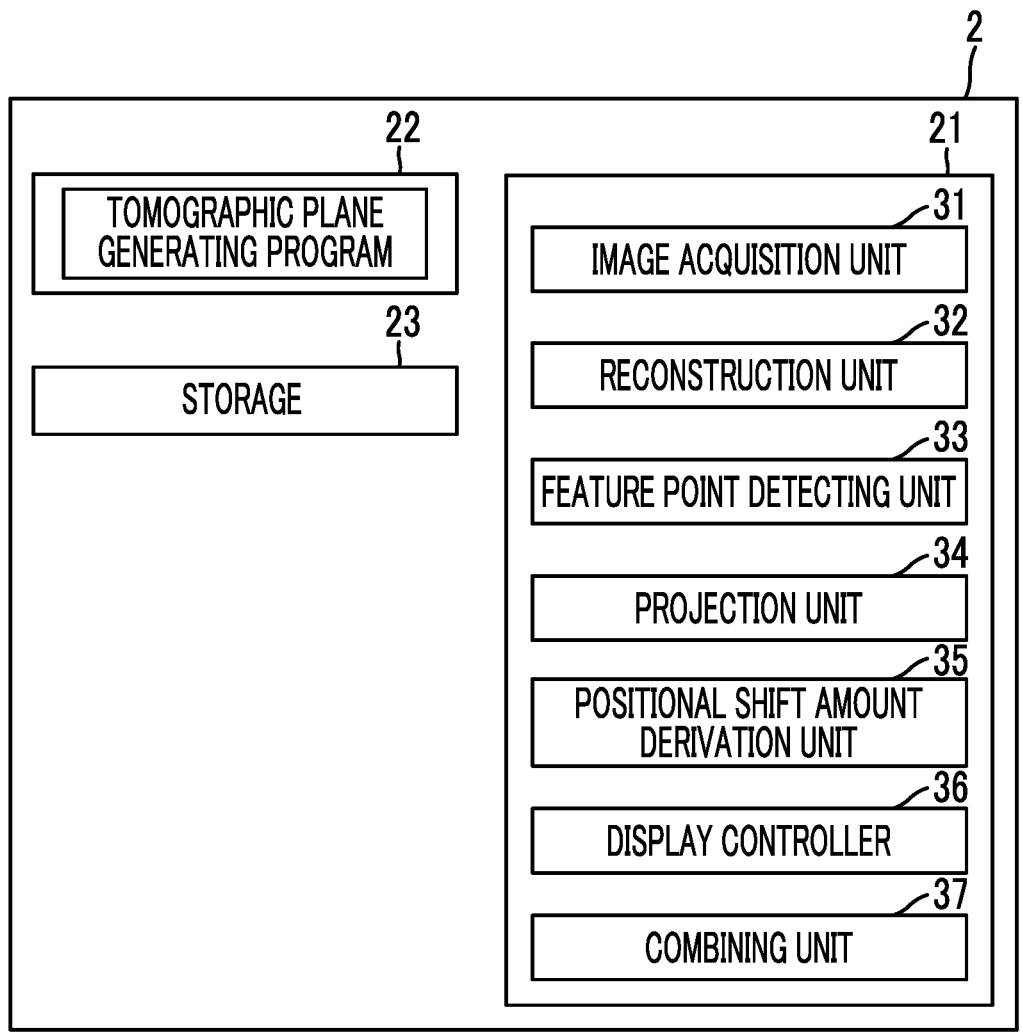
FIG. 21 is a diagram showing a schematic configuration of the tomographic image generating apparatus realized by installing a tomographic image generating program in a computer in a fourth embodiment.

Hereinafter, the fourth embodiment of the present disclosure will be described. FIG. 21 is a diagram showing a schematic configuration of the tomographic image generating apparatus realized by installing a tomographic image generating program in the computer 2 in the fourth embodiment. In FIG. 21, the same reference numbers as those in FIG. 3 are assigned to the same configurations as those in FIG. 3, and detailed description thereof will be omitted here. The fourth embodiment is different from the first embodiment in that the tomographic image generating apparatus further comprises a combining unit 37 that combines two or more tomographic images among the plurality of tomographic images, or at least one of the plurality of tomographic images and at least one of the plurality of projection images Gi to generate the composite two-dimensional image.

In the fourth embodiment, the combining unit 37 generates a composite two-dimensional image by using, for example, the method disclosed in JP2014-128716A. The method disclosed in JP2014-128716A is a method in which two or more tomographic images among the plurality of tomographic images, or at least one of the plurality of tomographic images and at least one of the plurality of projection images Gi are projected in the depth direction in which the tomographic planes of the subject are arranged to generate the composite two-dimensional image. The method of generating the composite two-dimensional image is not limited thereto. For example, the minimum value projection method may be performed with respect to two or more tomographic images among the plurality of tomographic images, or at least one of the plurality of tomographic images and at least one of the plurality of projection images Gi are projected in the depth direction in which the tomographic planes of the subject are arranged to generate the composite two-dimensional image.

In the fourth embodiment, the feature point detecting unit 33 first detects a two-dimensional feature point from the composite two-dimensional image. The detection of the two-dimensional feature point may be performed in the same manner as in the above embodiments. Then, the feature point detecting unit 33 detects the feature point corresponding to the two-dimensional feature point from the plurality of tomographic images Dj with reference to the depth map created in advance.

Figure 22:
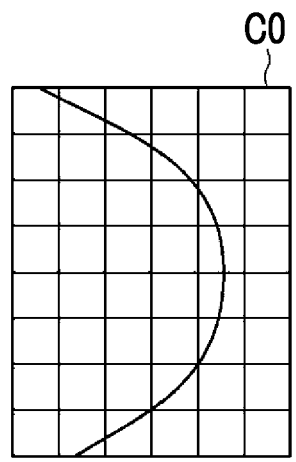
FIG. 22 is a diagram illustrating the generation of a feature point map.

The depth map is a map in which each position on the composite two-dimensional image is associated with the depth information indicating the position of the tomographic plane corresponding to each position. The depth map is created by using the method disclosed in WO2014/203531A in advance. In the method disclosed in WO2014/203531A, first, the composite two-dimensional image is divided into a plurality of local regions, and the correlation between the each region obtained by division and the plurality of tomographic images Dj. For example, as shown in FIG. 22, the composite two-dimensional image C0 is divided into 6×8 local regions, and the correlation between the plurality of tomographic images Dj and each of the divided regions is obtained. Then, the depth map is created by associating the depth of the tomographic image Dj including the region with the largest correlation from the reference position of the tomographic plane with the position of each region. The reference position need only be, for example, the contact surface of the breast M with the compression plate 17. Here, the position of the tomographic plane Tj in a case of generating the tomographic image Dj is known. Therefore, by referring to the depth map, the position of the tomographic plane corresponding to each local region in the composite two-dimensional image C0 can be specified.

In the fourth embodiment, the feature point detecting unit 33 identifies the tomographic plane of the detected two-dimensional feature point with reference to the depth map. Then, the feature point corresponding to the two-dimensional feature point is detected on the specified tomographic plane.

Here, the plurality of tomographic images Dj have a large amount of information, so the amount of calculation for detecting the feature points is large. In the fourth embodiment, the two-dimensional feature point is detected from the composite two-dimensional image C0, and the feature point corresponding to the two-dimensional feature point is detected from the plurality of tomographic images Dj with reference to the depth map. Therefore, in a case where the depth map is created in advance, the amount of calculation can be reduced and the feature point can be detected quickly.

In the fourth embodiment, the display controller 36 may display the composite two-dimensional image on the display unit 3 together with the corrected tomographic image.

Hereinafter, the fifth embodiment will be described. The configuration of the tomographic image generating apparatus according to the fifth embodiment is the same as the configuration of the tomographic image generating apparatus according to the first embodiment shown in FIG. 3, only the processing to be performed is different, and thus the detailed description of the apparatus is omitted. The fifth embodiment is different from the first embodiment in that the corrected tomographic image Dhj is used as a new tomographic image, and feature point detection, tomographic plane projection image acquisition, positional shift amount derivation, and new corrected tomographic image generation are repeated.

Figure 23:
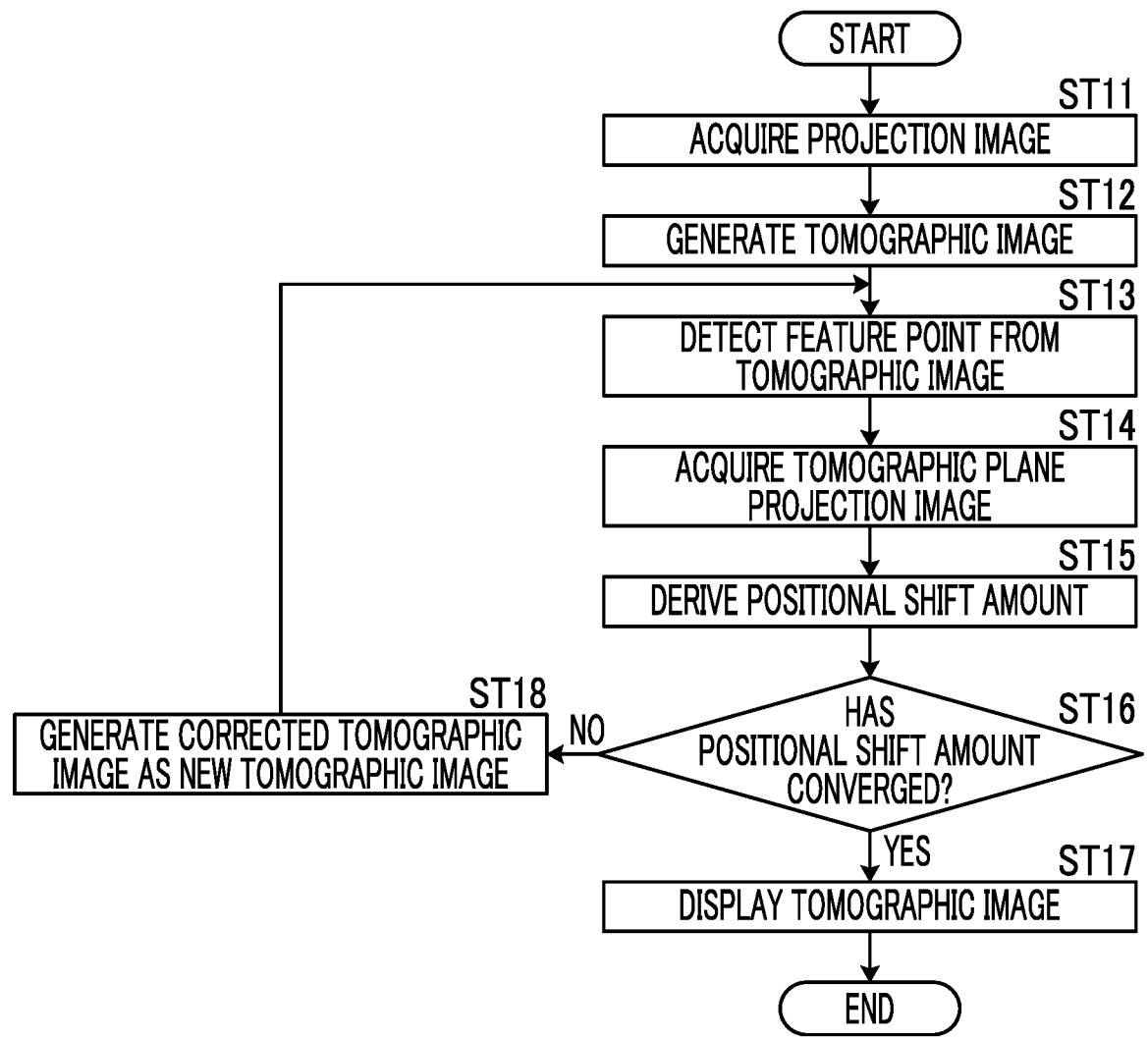
FIG. 23 is a flowchart showing a process performed in a fifth embodiment.

FIG. 23 is a flowchart showing a process performed in the fifth embodiment. In FIG. 23, the processing from step ST11 to step ST15 are the same as the processing from step ST1 to step ST5 shown in FIG. 16, so detailed description thereof will be omitted here. In a case where the positional shift amount is derived in step ST15, the positional shift amount derivation unit 35 determines whether the positional shift amount converges (step ST16). The determination of whether the positional shift amount converges may be performed by determining whether the positional shift amount derived for each tomographic plane projection image GTi is equal to or smaller than a predetermined threshold Th1. The threshold Th1 may be set to a value at which it can be said that there is no influence of body movement on the tomographic image without correcting the positional shift amount any more. The determination of whether the positional shift amount converges may be performed by determining whether the average value of the positional shift amounts derived for the plurality of tomographic plane projection image GTi is equal to or smaller than a predetermined threshold Th1. In a case of positive in step ST16, it is unnecessary to correct the positional shift amount, and thus the display controller 36 displays the tomographic image (step ST17), and the processing is terminated.

In a case of negative in step ST16, the reconstruction unit 32 reconstructs the plurality of projection images Gi while correcting the positional shift amount, and thereby generates a corrected tomographic image Dhj as a new tomographic image (step ST18). Returning to the processing of step ST13, the feature point detecting unit 33 detects the feature point from the plurality of new tomographic images, in step ST14, the projection unit 34 acquires a plurality of new tomographic plane projection images, and the positional shift amount derivation unit 35 derives a new positional shift amount between the plurality of new tomographic plane projection images in step ST15, and determines whether the positional shift amount is equal to or smaller than the predetermined threshold Th1 in step ST16. The processing of step ST18 and step ST13 to step ST15 is repeated until it is determined to be positive in step ST16. Also, in a case where the corrected tomographic image is generated as a new tomographic image, the tomographic image to be displayed in step ST17 is a new tomographic image.

As described above, in the fifth embodiment, the derivation of the new positional shift amount based on the new tomographic image is repeated until the positional shift amount converges. Therefore, the positional shift due to the body movement can be removed more appropriately and efficiently, and it possible to acquire a high-quality tomographic image in which the body movement is accurately corrected.

As described above, in the second embodiment to the fourth embodiment, the derivation of the new positional shift based on the new tomographic image may be repeated until the positional shift amount converges as in the fifth embodiment.

Figure 24:
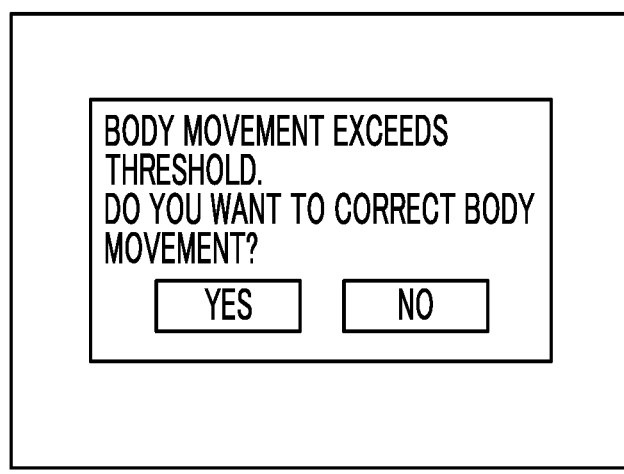
FIG. 24 is a diagram showing a warning display.

Further, in the above embodiments, the positional shift amount derived by the positional shift amount derivation unit 35 is compared with a predetermined threshold, and only in a case where the positional shift amount exceeds the threshold value, the tomographic image may be reconstructed while correcting the positional shift amount. The threshold may be set to a value at which it can be said that there is no influence of body movement on the tomographic image without correcting the positional shift amount. In this case, as shown in FIG. 24, a warning display 45 for notifying that the body movement exceeds the threshold may be displayed on the display unit 3. The operator can instruct whether to perform body movement correction by selecting YES or NO on the warning display 45.

In the above embodiments, in order to easily derive the positional shift amount and the temporary positional shift amount, the regions of interest are set in the tomographic image Dj and the tomographic plane projection image GTi, and the movement direction and the movement amount of the region of interest is derived as the shift vector, that is, the positional shift amount and the temporary positional shift amount, but the present invention is not limited thereto. The positional shift amount may be derived without setting the region of interest.

Figure 25:
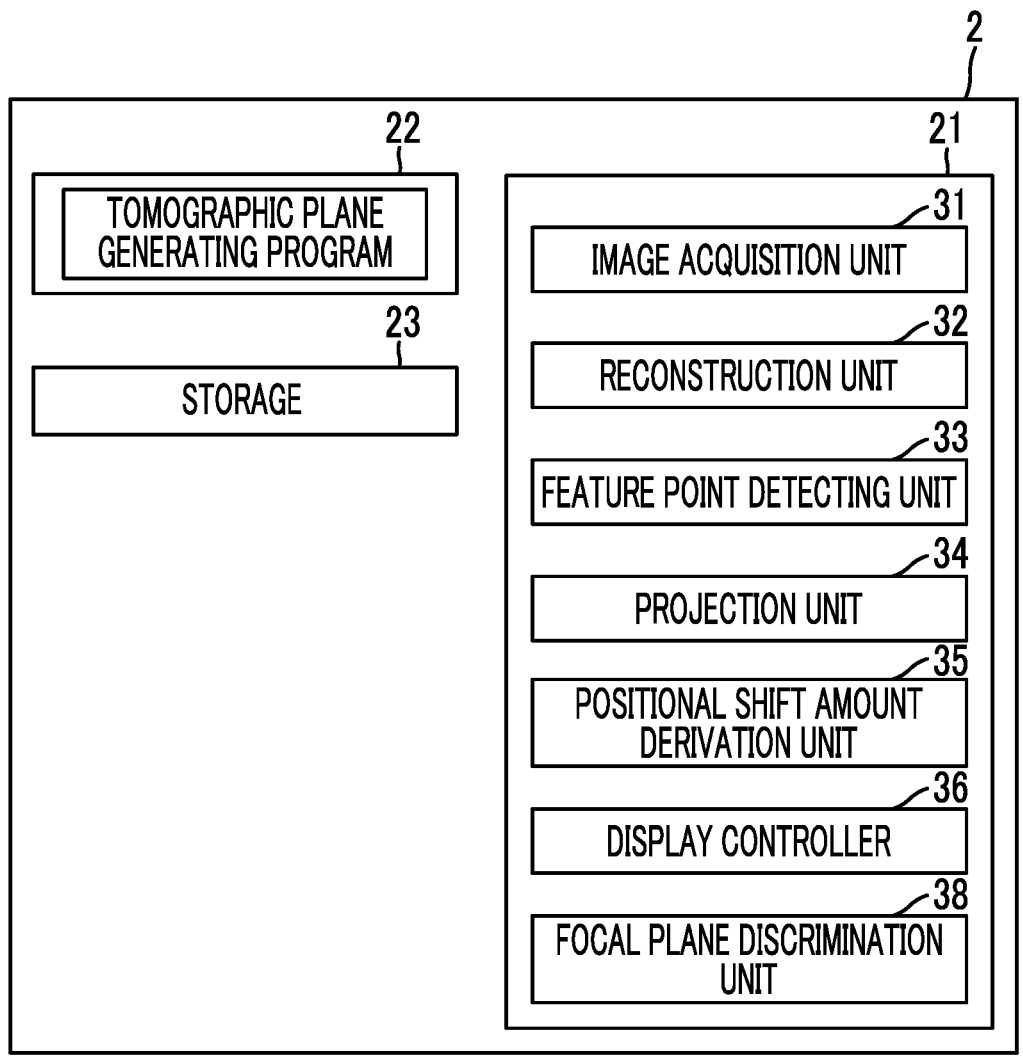
FIG. 25 is a diagram showing a schematic configuration of the tomographic image generating apparatus realized by installing a tomographic image generating program in a computer in a sixth embodiment.

Hereinafter, the sixth embodiment of the present disclosure will be described. FIG. 25 is a diagram showing a schematic configuration of the tomographic image generating apparatus realized by installing a tomographic image generating program in the computer 2 in the sixth embodiment. In FIG. 25, the same reference numbers as those in FIG. 3 are assigned to the same configurations as those in FIG. 3, and detailed description thereof will be omitted here. The sixth embodiment is different from the first embodiment in that the tomographic image generating apparatus according to the sixth embodiment further comprises a focal plane discrimination unit 38 that discriminates whether the corresponding tomographic plane corresponding to the tomographic image in which each of the plurality of feature points F is detected is a focal plane, and the positional shift amount derivation unit 35 derives the positional shift amount on the corresponding tomographic plane which is discriminated to be the focal plane. The processing according to the sixth embodiment can be applied to the second to fifth embodiments, but only the case where the processing is applied to the first embodiment will be described here.

Figure 26:
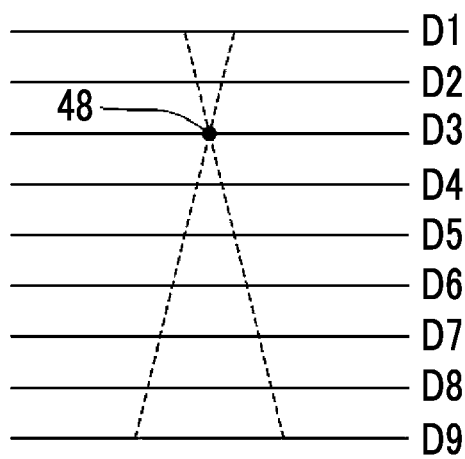
FIG. 26 is a diagram illustrating a ripple artifact.

Here, in the tomographic image acquired by tomosynthesis imaging, the structure glare occurs in the tomographic image other than the tomographic image in which the structure exists. This is called a ripple artifact. FIG. 26 is a diagram illustrating a ripple artifact. As shown in FIG. 26, assuming that a certain structure 48 is included in the tomographic image D3, the tomographic image corresponding to the upper and lower tomographic planes of the tomographic image D3 includes the ripple artifact of the structure 48. The ripple artifact becomes wider and blurry as the distance from the tomographic plane including the structure 48 increases. The range in which the ripple artifact spreads corresponds to the range in which the X-ray source 16 moves.

Here, in a case where the feature point F detected by the feature point detecting unit 33 from the tomographic image Dj of the corresponding tomographic plane is the ripple artifact, the feature point F is blurred and spreads over a wide area. Therefore, in a case where such a feature point F is used, the positional shift amount cannot be derived accurately.

Therefore, in the sixth embodiment, the focal plane discrimination unit 38 discriminates whether the corresponding tomographic plane the feature point F is detected is a focal plane, the projection unit 34 generates the tomographic plane projection image GTi on the corresponding tomographic plane which is discriminated to be the focal plane, and the positional shift amount derivation unit 35 derives the positional shift amount. Specifically, the positional shift amount is derived using the feature point detected on the corresponding tomographic plane discriminated to be the focal plane. Hereinafter, the discrimination of whether the corresponding tomographic plane is the focal plane will be described.

Figure 27:
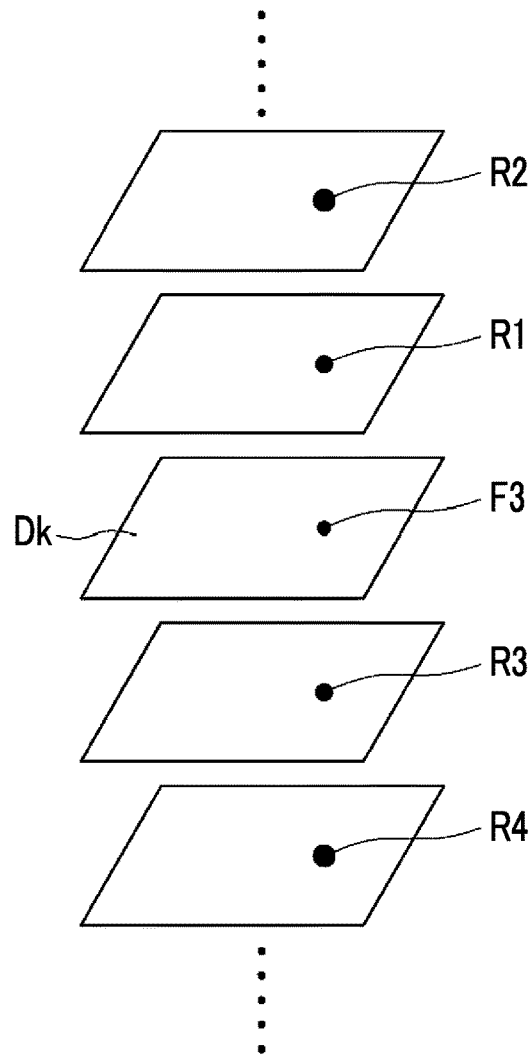
FIG. 27 is a diagram illustrating the derivation of correspondence points.
Figure 28:
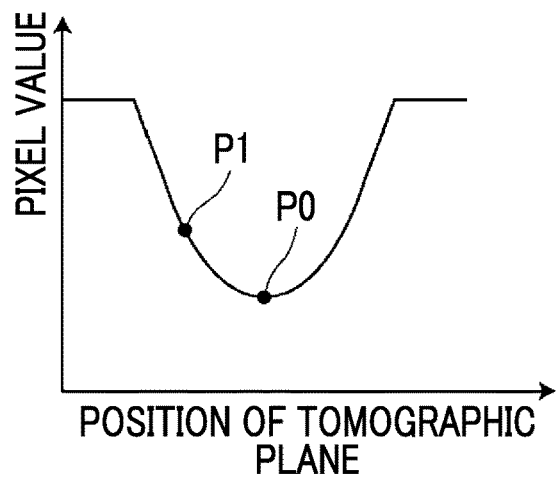
FIG. 28 is a diagram showing a result of plotting pixel values of the feature points and the correspondence points.

The focal plane discrimination unit 38 derives the correspondence point corresponding to the feature point in the plurality of tomographic images for the feature point detected by the feature point detecting unit 33. FIG. 27 is a diagram illustrating the derivation of correspondence points. As shown in FIG. 27, assuming that the feature point F3 is detected in a certain tomographic image Dk, the positional shift amount derivation unit 35 derives the correspondence points R1, R2, R3, R4, . . . corresponding to the feature point F3 in the plurality of tomographic images positioned in the thickness direction of the tomographic image Dk. In the following description, the reference code of the correspondence point is R. The correspondence point R need only be derived by registration of the region of interest including the feature point F3 with the tomographic image other than the tomographic image Dk. Then, the focal plane discrimination unit 38 plots the pixel values of the feature point F3 and the correspondence point R in the order in which the tomographic planes are arranged. FIG. 28 is a diagram showing a result of plotting pixel values of the feature points and the correspondence points. As shown in FIG. 28, the pixel values of the feature point and the correspondence point change so as to have a minimum value at the feature point due to the influence of the ripple artifact. Here, in a case where the feature point F3 is on the focal plane, the feature point F3 is not blurred, and the brightness is high, that is, the pixel value is small. On the other hand, in a case where the feature point F3 is not on the focal plane, the feature point F3 is the ripple artifact, so that the pixel value is blurred and the pixel value is larger than the minimum value.

Therefore, the focal plane discrimination unit 38 discriminates that the corresponding tomographic plane in which the feature point F3 is detected is the focal plane in a case where the position of the tomographic plane in which the feature point F3 is detected is the position P0 shown in FIG. 28 where the pixel value is the minimum in the result of plotting the pixel values of the feature point F3 and the correspondence point. On the other hand, the focal plane discrimination unit 38 discriminates that the corresponding tomographic plane in which the feature point F3 is detected is not the focal plane in a case where the position of the tomographic plane where the feature point F3 is detected is the position P1 or the like shown in FIG. 28 where the pixel value is not the minimum.

The projection unit 34 generates the tomographic plane projection image GTi only on the corresponding tomographic plane discriminated to be the focal plane, as in the above embodiments. The positional shift amount derivation unit 35 derives the positional shift amount of the tomographic plane projection image GTi on the corresponding tomographic plane discriminated to be the focal plane. That is, the positional shift amount derivation unit 35 derives the positional shift amount of the tomographic plane projection image GTi by using the feature point detected on the corresponding tomographic plane discriminated to be the focal plane.

Figure 29:
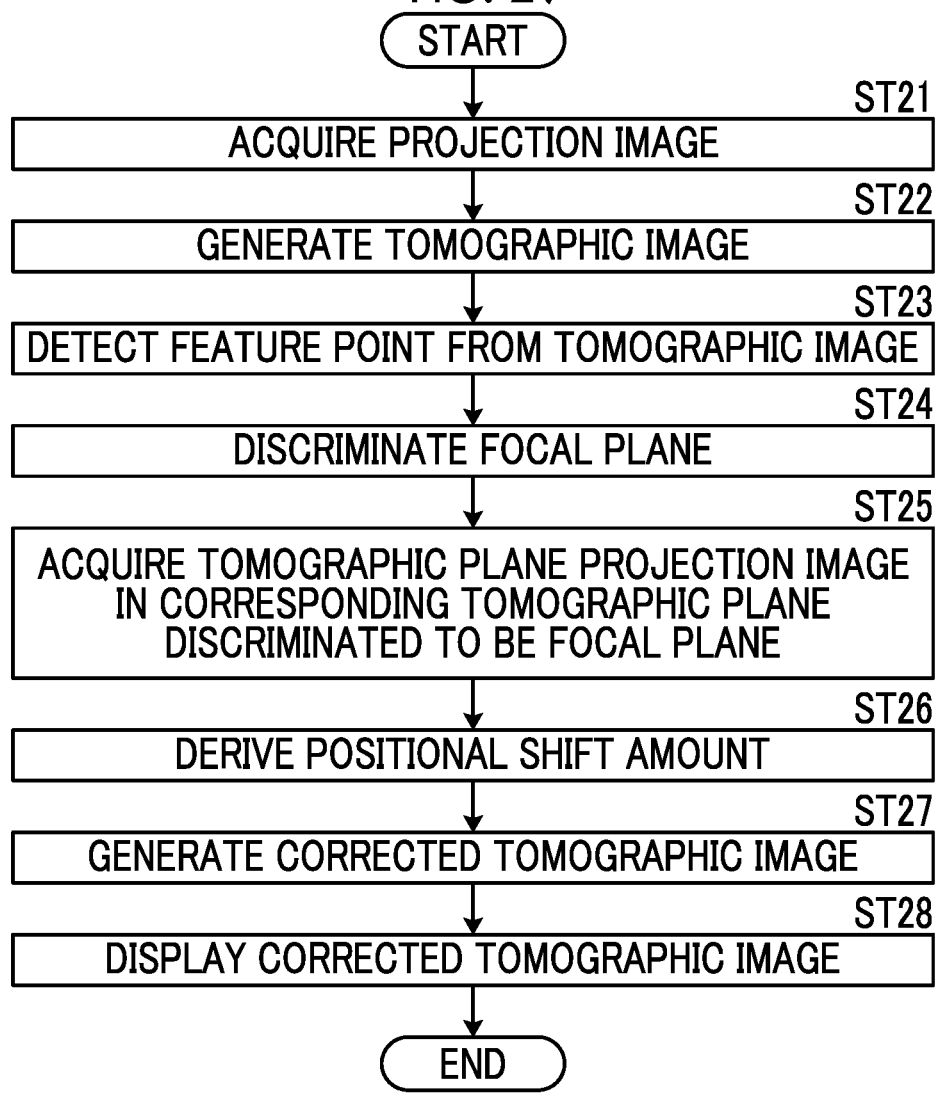
FIG. 29 is a flowchart showing a process performed in the sixth embodiment.

Next, the processing performed in the sixth embodiment will be described. FIG. 29 is a flowchart showing a process performed in the sixth embodiment. In FIG. 29, the processing from step ST21 to step ST23 are the same as the processing from step ST1 to step ST3 shown in FIG. 16, so detailed description thereof will be omitted here. In the sixth embodiment, it is assumed that the plurality of feature points are detected. In a case where the feature point detecting unit 33 detects the plurality of feature points, the focal plane discrimination unit 38 discriminates whether the corresponding tomographic plane corresponding to the tomographic image in which each of the plurality of feature points detected by the feature point detecting unit 33 is detected is the focal plane (focal plane discrimination; step ST24). The projection unit 34 generates the tomographic plane projection image GTi on the corresponding tomographic plane discriminated to be the focal plane (step ST25), and the positional shift amount derivation unit 35 derives the positional shift amount by using the feature point detected in the corresponding tomographic plane discriminated to be the focal plane (step ST26).

Further, the reconstruction unit 32 reconstructs the plurality of projection images Gi while correcting the positional shift amount, and thereby generates a corrected tomographic image Dhj (step ST27). Then, the display controller 36 displays the corrected tomographic image Dhj on the display unit 3 (step ST28), and the processing is terminated. The generated corrected tomographic image Dhj is transmitted to the external storage device (not shown) and stored.

As described above, in the sixth embodiment, the positional shift amount is derived on the corresponding tomographic plane discriminated to be the focal plane. Therefore, the positional shift amount can be derived accurately without being affected by the ripple artifact, and as a result, the corrected tomographic image Dhj in which the positional shift is accurately corrected can be generated.

In the sixth embodiment, discrimination is made as to whether the corresponding tomographic plane is the focal plane by using the plot results of the pixel values of the feature point and the correspondence point, but the discrimination of the focal plane is not limited thereto. Regarding the feature point and the ripple artifact, the difference in contrast of the feature point with the peripheral pixels is larger. Therefore, the contrasts of the feature point and the correspondence point with the peripheral pixels are derived, and in a case where the contrast of the feature point is the maximum, the corresponding tomographic plane in which the feature point is detected may be discriminated to be the focal plane. Further, the pixel value of the position corresponding to the feature point in the projection image has a small variation between the projection images in a case where the feature point is on the focal plane, but in a case where the feature point is not on the focal plane, the projection image may represent the structure other than the structure corresponding to the feature point, so the variation between the projection images is large. Therefore, the variance value of the pixel value corresponding to the feature point between the projection images Gi is derived, and in a case where the variance value is equal to or smaller than a predetermined threshold, the corresponding tomographic plane in which the feature point is detected may be discriminated to be the focal plane. Also, the focal plane discrimination unit 38 may include a discriminator that is machine learned such that in a case where the pixel values of the feature point and surrounding of the feature point are input, the discrimination result is output as to whether the corresponding tomographic plane in which the feature point is detected is the focal plane. The discriminator may discriminate whether the corresponding tomographic plane in which the feature point is detected is the focal plane.

Figure 30:
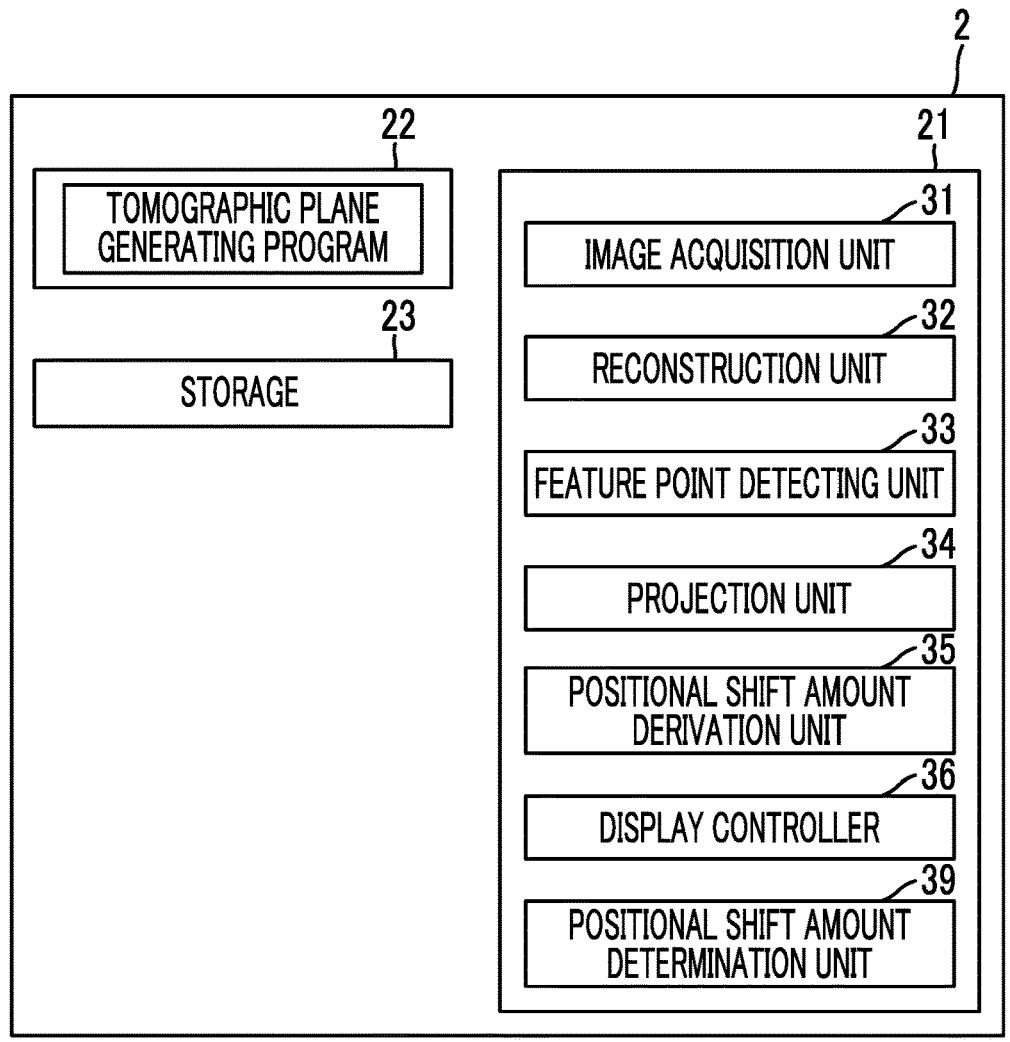
FIG. 30 is a diagram showing a schematic configuration of the tomographic image generating apparatus realized by installing a tomographic image generating program in a computer in a seventh embodiment.

Hereinafter, the seventh embodiment of the present disclosure will be described. FIG. 30 is a diagram showing a schematic configuration of the tomographic image generating apparatus realized by installing a tomographic image generating program in the computer 2 in the seventh embodiment. In FIG. 30, the same reference numbers as those in FIG. 3 are assigned to the same configurations as those in FIG. 3, and detailed description thereof will be omitted here. The seventh embodiment is different from the first embodiment in that the tomographic image generating apparatus further comprises a positional shift amount determination unit 39 that performs image quality evaluation for a region of interest including the feature point in the corrected tomographic image Dhj, and determines whether the derived positional shift amount is appropriate or inappropriate based on a result of the image quality evaluation. The processing according to the seventh embodiment can be applied to the second to sixth embodiments, but only the case where the processing is applied to the first embodiment will be described here.

Figure 31:
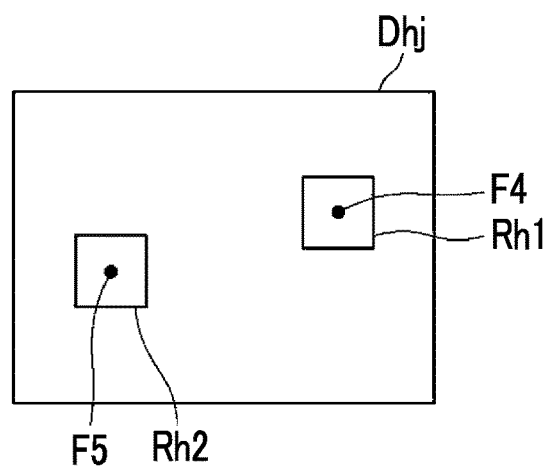
FIG. 31 is a diagram illustrating the setting of a region of interest in the seventh embodiment.

The positional shift amount determination unit 39 sets, for the image quality evaluation, the regions of interest Rh1 and Rh2 centered on the coordinate positions of the plurality (here, two) of the feature points F4 and F5 included in the corrected tomographic image Dhj shown in FIG. 31. Then, a high-frequency image is generated by extracting high-frequency components in each of the regions of interest Rh1 and Rh2. The extraction of the high-frequency components need only be performed by performing the filtering processing using the Laplacian filter to generate a secondary differential image, but the present invention is not limited thereto. The positional shift amount determination unit 39 derives the magnitudes of the high-frequency components of the regions of interest Rh1 and Rh2. The magnitude of the high-frequency components need only be derived by the sum of squares of the pixel value of the high-frequency image, but the present invention is not limited thereto. The positional shift amount determination unit 39 derives the sum of the magnitudes of the high-frequency components of all of the regions of interest Rh1 and Rh2.

In a case where the positional shift correction is appropriately performed by deriving the positional shift amount appropriately, the image blurriness of the corrected tomographic image Dhj decreases, and the high-frequency components increase. On the other hand, in a case where the positional shift correction is inappropriate due to the inappropriate derived positional shift amount, the image blurriness of the corrected tomographic image Dhj increases, and the high-frequency components decrease. Therefore, in the seventh embodiment, the positional shift amount determination unit 39 performs the image quality evaluation based on the magnitude of the high-frequency components. That is, the positional shift amount determination unit 39 determines whether the sum of the magnitudes of the high-frequency components of all of the regions of interest Rh1 and Rh2, which are derived as above, is equal to or larger than the predetermined threshold Th2. In a case where the sum is equal to or larger than the threshold Th2, the positional shift amount determination unit 39 determines that the positional shift amount is appropriate, and in a case where the sum is smaller than the threshold Th2, the positional shift amount determination unit 39 determines that the positional shift amount is inappropriate. In a case where the positional shift amount determination unit 39 determines that the positional shift amount is inappropriate, the display controller 36 displays the tomographic image Dj before correction on the display unit 3 instead of the corrected tomographic image Dhj. In this case, instead of the corrected tomographic image Dhj, the tomographic image Dj before correction is transmitted to the external storage device.

Figure 32:
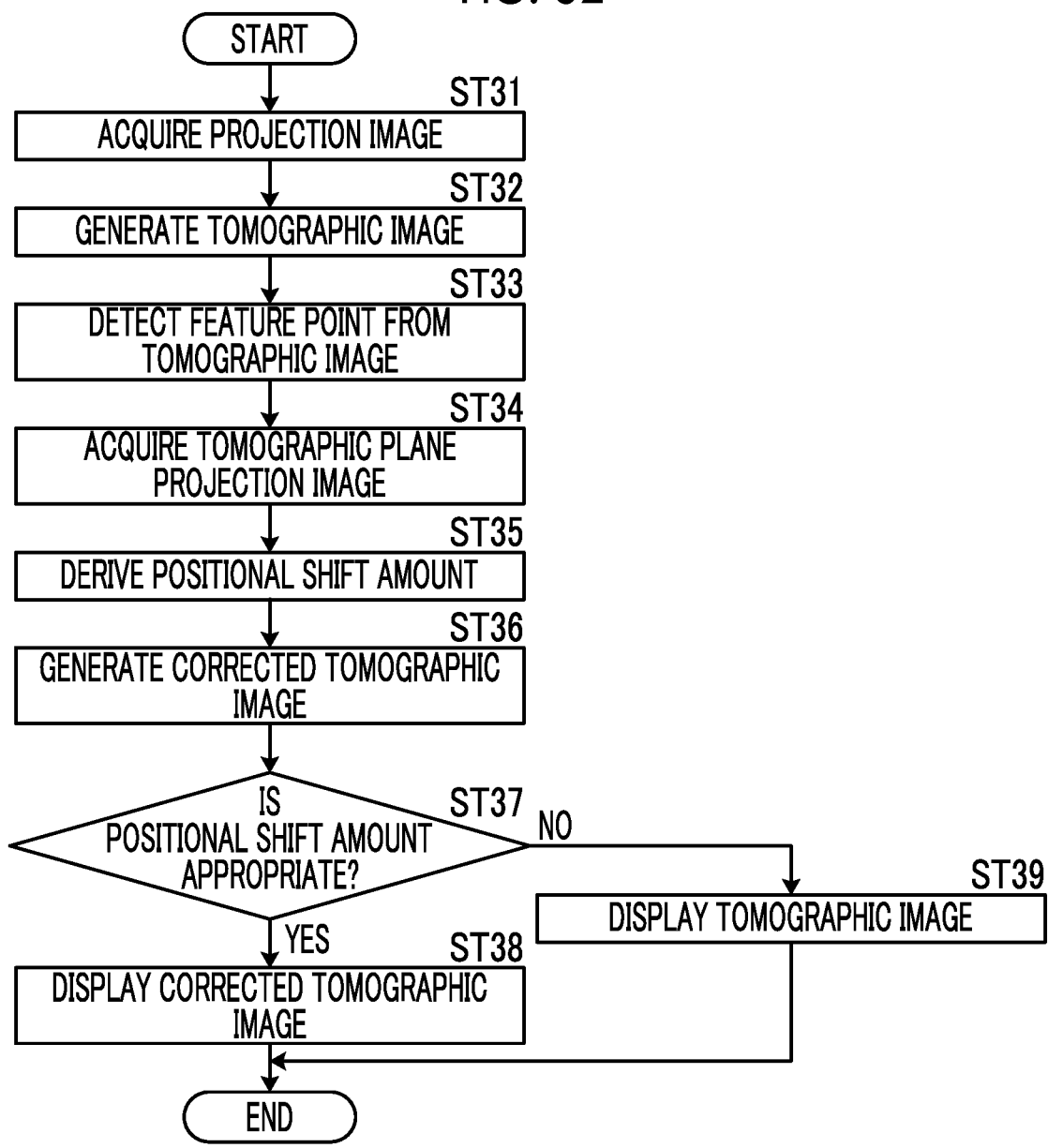
FIG. 32 is a flowchart showing a process performed in the seventh embodiment.

Next, the processing performed in the seventh embodiment will be described. FIG. 32 is a flowchart showing a process performed in the seventh embodiment. In FIG. 32, the processing from step ST31 to step ST36 are the same as the processing from step ST1 to step ST6 shown in FIG. 16, so detailed description thereof will be omitted here. In a case where the reconstruction unit 32 generates the corrected tomographic image Dhj, the positional shift amount determination unit 39 performs image quality evaluation for a region of interest including the feature point in the corrected tomographic image Dhj, and determines whether the derived positional shift amount is appropriate or inappropriate based on a result of the image quality evaluation (step ST37).

In a case where the positional shift amount is appropriate, the display controller 36 displays the corrected tomographic image Dhj on the display unit 3 (step ST38), and the processing is terminated. The generated corrected tomographic image Dhj is transmitted to the external storage device (not shown) and stored. On the other hand, in a case where the positional shift amount is inappropriate, the display controller 36 displays the tomographic image Dj on the display unit 3 (step ST39), and the processing is terminated. In this case, the tomographic image Dj is transmitted to the external storage device (not shown) and stored.

In a case where the positional shift amount is derived by the positional shift amount derivation unit 35, an appropriate positional shift amount may not be derived due to the influence of the structure other than the feature point. In the seventh embodiment, the image quality evaluation is performed on the corrected tomographic image Dhj, and the determination is made as to whether the positional shift amount is appropriate or inappropriate based on the result of the image quality evaluation. Therefore, it is possible to appropriately determine whether the derived positional shift amount is appropriate or inappropriate. Also, the tomographic image Dj before correction is displayed or stored in a case where the determination is made that the positional shift amount is inappropriate, it is possible to reduce the possibility of making an erroneous diagnosis due to the corrected tomographic image Dhj generated based on the inappropriate positional shift amount.

In the seventh embodiment, the image quality evaluation is performed based on the magnitude of the high-frequency components of the region of interest set in the corrected tomographic image Dhj, but the present invention is not limited thereto. The positional shift amount determination unit 39 may perform the image quality evaluation for the region of interest including the feature point in the tomographic image Dj, compare the result of the image quality evaluation for the corrected tomographic image Dhj with a result of the image quality evaluation for the tomographic image Dj, and decide the tomographic image with a better result of the image quality evaluation as a final tomographic image. Here, the final tomographic image is the tomographic image that is displayed on the display unit 3, or transmitted and stored in the external device.

As described above, in the sixth embodiment to the seventh embodiment, the derivation of the new positional shift based on the new tomographic image may be repeated until the positional shift amount converges as in the fifth embodiment.

Further, also in the sixth embodiment and the seventh embodiment, the positional shift amount derived by the positional shift amount derivation unit 35 is compared with a predetermined threshold, and only in a case where the positional shift amount exceeds the threshold value, the tomographic image may be reconstructed while correcting the positional shift amount.

Figure 33:
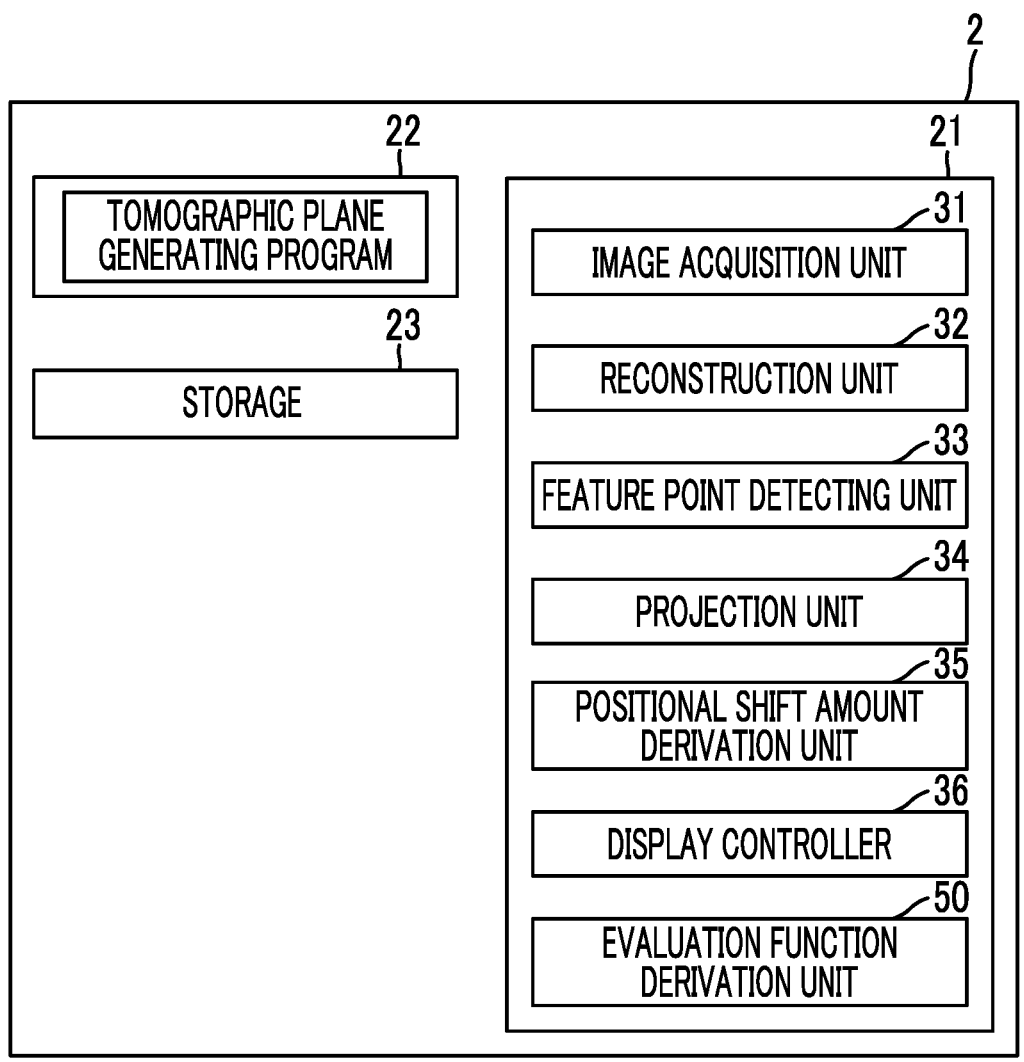
FIG. 33 is a diagram showing a schematic configuration of the tomographic image generating apparatus realized by installing a tomographic image generating program in a computer in an eighth embodiment.

Hereinafter, the eighth embodiment of the present disclosure will be described. FIG. 33 is a diagram showing a schematic configuration of the tomographic image generating apparatus realized by installing a tomographic image generating program in the computer 2 in the eighth embodiment. In FIG. 33, the same reference numbers as those in FIG. 3 are assigned to the same configurations as those in FIG. 3, and detailed description thereof will be omitted here. The eighth embodiment is different from the first embodiment in that the tomographic image generating apparatus further comprises an evaluation function derivation unit 50 that derives an evaluation function for performing image quality evaluation for a region of interest including the feature point in the corrected tomographic image Dhj, and the positional shift amount derivation unit 35 derives the positional shift amount for optimizing the evaluation function. The processing according to the eighth embodiment can be applied to the second to sixth embodiments, but only the case where the processing is applied to the first embodiment will be described here.

In the eighth embodiment, the evaluation function derivation unit 50 generates the high-frequency image for the region of interest corresponding to the feature point F, which is set with respect to the tomographic plane projection image GTi by the positional shift amount derivation unit 35. The generation of the high-frequency image need only be performed, as in the positional shift amount determination unit 39 according to the seventh embodiment, by performing the filtering processing using the Laplacian filter to generate a secondary differential image. The pixel value of the derived high-frequency image in the region of interest is referred to as qkl. k represents the k-th projection image, and l represents the number of pixels in the region of interest.

Here, the transformation matrix for correcting the positional shift amount is Wk, and the transformation parameter in the transformation matrix is $\theta k$. The transformation parameter $\theta k$ corresponds to the positional shift amount. In this case, the image quality evaluation value of the region of interest corresponding to the feature point F in the corrected tomographic image Dhj can be regarded as an added value of the magnitudes of the high-frequency image of the region of interest after positional shift correction in each of the projection images Gi. By deriving the transformation parameter $\theta k$, that is, the positional shift amount so that the added value is maximum, it is possible to generate the corrected tomographic image Dhj in which the positional shift amount is appropriately corrected.

Therefore, the evaluation function derivation unit 50 derives the evaluation function shown in Equation (3) below. The evaluation function Ec shown in Equation (3) is an evaluation function Ec to obtain the transformation parameter θk for minimizing the value in parentheses on the right side with a minus in order to maximize the above addition result. The evaluation function shown in Equation (3) has a plurality of local solutions. Therefore, a constraint condition is applied to the range and the average value of the transformation parameter θk. For example, a constraint condition is applied such that the average of the transformation parameters θk for all of the projection images is 0. More specifically, in a case where the transformation parameter θk is a movement vector representing parallel movement, a constraint condition is applied in which the average value of the movement vectors for all of the projection images Gi is set to 0. Then, in the eighth embodiment, the positional shift amount derivation unit 35 derives the transformation parameter θk to minimize the evaluation function Ec shown in Equation (3) below, that is, the positional shift amount.

$$Ec = \arg\min_{\theta}\left(-\sum_{k}\sum_{l \in ROI}(Wk(\theta k)qkl)^2\right) \quad (3)$$

As described above, in the eighth embodiment, the tomographic image generating apparatus further comprises an evaluation function derivation unit 50 that derives an evaluation function for performing image quality evaluation for a region of interest including the feature point in the corrected tomographic image Dhj, and the positional shift amount derivation unit 35 derives the positional shift amount for optimizing the evaluation function. Therefore, it is possible to reduce the possibility that an erroneous diagnosis is made by the corrected tomographic image Dhj generated based on the inappropriate positional shift amount.

In the above embodiments, in order to easily derive the positional shift amount and the temporary positional shift amount, the regions of interest are set in the tomographic image Dj and the tomographic plane projection image GTi, and the movement direction and the movement amount of the region of interest is derived as the shift vector, that is, the positional shift amount and the temporary positional shift amount, but the present invention is not limited thereto. The positional shift amount may be derived without setting the region of interest.

Further, in the above embodiments, the tomographic plane projection image GTi is acquired by the projection unit 34, and the positional shift amount between the tomographic plane projection images GTi is derived by the positional shift amount derivation unit 35, but the present invention is limited to thereto. The positional shift amount between the projection images Gi may be derived without acquiring the tomographic plane projection image GTi. In this case, the projection unit 34 is unnecessary in the above embodiments. The positional shift amount derivation unit 35 need only derive the positional shift amount based on the positional relationship of the projection images Gi on the corresponding tomographic plane corresponding to the tomographic image in which the feature point F is detected.

In the embodiments described above, the subject is the breast M, but the present invention is not limited thereto. It is needless to say that any part such as the chest or the abdomen of the human body may be the subject.

In the embodiments described above, for example, various processors shown below can be used as the hardware structures of processing units that execute various kinds of processing, such as the image acquisition unit 31, the reconstruction unit 32, the feature point detecting unit 33, the projection unit 34, the positional shift amount derivation unit 35, the display controller 36, the combining unit 37, the focal plane discrimination unit 38, the positional shift amount determination unit 39, and the evaluation function derivation unit 50. The various processors include not only the above-described CPU, which is a general-purpose processor that executes software (program) and functions as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of the various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units by one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by one or more of the above-described various processors as a hardware structure.

More specifically, as the hardware structure of these various processors, it is possible to use an electrical circuit (circuitry) in which circuit elements such as semiconductor elements are combined.

What is claimed is:

1. A tomographic image generating apparatus comprising at least one processor,
   wherein the processor is configured to:
   acquire a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;
   reconstruct all or a part of the plurality of projection images to generate a tomographic image on each of a plurality of tomographic planes of the subject;
   detect at least one feature point from a plurality of the tomographic images;
   project the plurality of projection images on a corresponding tomographic plane corresponding to the tomographic image in which the feature point is detected based on a positional relationship between the radiation source position and the radiation detector in a case of imaging the plurality of projection images to acquire a tomographic plane projection image corresponding to each of the plurality of projection images; and
   set a plurality of first local regions including the feature point in the plurality of tomographic plane projection images, set a second local region including the feature point in the tomographic image in which the feature point is detected, derive a positional shift amount of each of the plurality of first local regions with respect to the second local region as a temporary positional shift amount, and derive a positional shift amount between the plurality of projection images based on body movement of the subject based on the plurality of the temporary positional shift amounts, wherein the processor is further configured to reconstruct the plurality of projection images excluding a target projection image which corresponds to a target tomographic plane projection image of which the positional shift amount is to be derived, and generate the plurality of tomographic images as target tomographic images, and derive the positional shift amount of the target tomographic plane projection image by using the target tomographic images.

2. The tomographic image generating apparatus according to claim 1, wherein the processor is further configured to reconstruct the plurality of projection images by correcting the positional shift amount to generate a corrected tomographic image on at least one tomographic plane of the subject.

3. The tomographic image generating apparatus according to claim 1, wherein the processor is configured to derive the temporary positional shift amount based on a peripheral region of the feature point in the second local region.

4. A tomographic image generating apparatus comprising at least one processor, wherein the processor is configured to:

acquire a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

reconstruct all or a part of the plurality of projection images to generate a tomographic image on each of a plurality of tomographic planes of the subject;

detect a plurality of feature point from a plurality of the tomographic images;

discriminate whether the corresponding tomographic plane corresponding to the tomographic image in which each of the plurality of feature points is detected is a focal plane, and derive a positional shift amount between the plurality of projection images based on body movement of the subject with the feature point as a reference on a corresponding tomographic plane which is discriminated to be the focal plane.

5. The tomographic image generating apparatus according to claim 4, wherein the processor is further configured to reconstruct the plurality of projection images by correcting the positional shift amount to generate a corrected tomographic image on at least one tomographic plane of the subject.

6. A tomographic image generating apparatus comprising at least one processor, wherein the processor is configured to:

acquire a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

reconstruct all or a part of the plurality of projection images to generate a tomographic image on each of a plurality of tomographic planes of the subject;

detect at least one feature point from a plurality of the tomographic images; and derive a positional shift amount between the plurality of projection images based on body movement of the subject with the feature point as a reference on a corresponding tomographic plane corresponding to the tomographic image in which the feature point is detected, wherein the processor is further configured to reconstruct the plurality of projection images by correcting the positional shift amount to generate a corrected tomographic image on at least one tomographic plane of the subject, and wherein the processor is further configured to perform image quality evaluation for a region of interest including the feature point in the corrected tomographic image, and determines whether the derived positional shift amount is appropriate or inappropriate based on a result of the image quality evaluation.

7. The tomographic image generating apparatus according to claim 6, wherein the processor is configured to perform the image quality evaluation for the region of interest including the feature point in the tomographic image, compares the result of the image quality evaluation for the corrected tomographic image with a result of the image quality evaluation for the tomographic image, and decides the tomographic image with a better result of the image quality evaluation as a final tomographic image.

8. A tomographic image generating apparatus comprising at least one processor, wherein the processor is configured to:

acquire a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

reconstruct all or a part of the plurality of projection images to generate a tomographic image on each of a plurality of tomographic planes of the subject;

detect at least one feature point from a plurality of the tomographic images; and derive a positional shift amount between the plurality of projection images based on body movement of the subject with the feature point as a reference on a corresponding tomographic plane corresponding to the tomographic image in which the feature point is detected, wherein the processor is further configured to reconstruct the plurality of projection images by correcting the positional shift amount to generate a corrected tomographic image on at least one tomographic plane of the subject, and wherein the processor is further configured to derive an evaluation function for performing image quality evaluation for a region of interest including the feature point in the corrected tomographic image, and derive the positional shift amount for optimizing the evaluation function.

9. The tomographic image generating apparatus according to claim 4, wherein the processor is configured to project the plurality of projection images on the corresponding tomographic plane based on a positional relationship between the radiation source position and the radiation detector in a case of imaging the plurality of projection images to acquire a tomographic plane projection image corresponding to each of the plurality of projection images, derive, as the positional shift amount between the plurality of projection images, a positional shift amount between a plurality of the tomographic plane projection images based on the body movement of the subject with the feature point as a reference on the corresponding tomographic plane.

10. The tomographic image generating apparatus according to claim 9, wherein the processor is further configured to set a local region corresponding to the feature point in the plurality of tomographic plane projection images, and derives the positional shift amount based on the local region.

11. The tomographic image generating apparatus according to claim 1, wherein the subject is a breast.

12. A tomographic image generating apparatus comprising at least one processor, wherein the processor is configured to:

acquire a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

reconstruct all or a part of the plurality of projection images to generate a tomographic image on each of a plurality of tomographic planes of the subject;

detect at least one feature point from a plurality of the tomographic images; and derive a positional shift amount between the plurality of projection images based on body movement of the subject with the feature point as a reference on a corresponding tomographic plane corresponding to the tomographic image in which the feature point is detected, wherein the subject is a breast, and wherein the processor is further configured to change a search range in a case of deriving the positional shift amount depending on at least one of a density of a mammary gland, a size of the breast, an imaging time of the tomosynthesis imaging, a compression pressure of the breast in a case of the tomosynthesis imaging, or an imaging direction of the breast.

13. The tomographic image generating apparatus according to claim 12, wherein the processor is further configured to reconstruct the plurality of projection images by correcting the positional shift amount to generate a corrected tomographic image on at least one tomographic plane of the subject.

14. The tomographic image generating apparatus according to claim 1, wherein the processor is further configured to combine two or more tomographic images among the plurality of tomographic images to generate a composite two-dimensional image, and detect a two-dimensional feature point in the composite two-dimensional image, and detects the feature point corresponding to the two-dimensional feature point from the plurality of tomographic images.

15. The tomographic image generating apparatus according to claim 1, wherein the processor is further configured to reconstruct all or a part of the plurality of projection images while correcting the positional shift amount to generate a plurality of the corrected tomographic images on the plurality of tomographic planes of the subject as a plurality of new tomographic images, detect the feature point from the plurality of new tomographic images, derive a new positional shift amount between the plurality of new projection images, and reconstruct the plurality of projection images while correcting the new positional shift amount to generate a new corrected tomographic image on at least one tomographic plane of the subject.

16. The tomographic image generating apparatus according to claim 15, wherein the processor is further configured to repeat generating of the new tomographic image, detecting of the feature point from the new tomographic image, and deriving of the new positional shift amount until the new positional shift amount converges.

17. A tomographic image generating method comprising:

acquiring a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

reconstructing all or a part of the plurality of projection images to generate a tomographic image on each of a plurality of tomographic planes of the subject;

detecting a plurality of feature point from a plurality of the tomographic images;

discriminating whether the corresponding tomographic plane corresponding to the tomographic image in which each of the plurality of feature points is detected is a focal plane, and deriving a positional shift amount between the plurality of projection images based on body movement of the subject with the feature point as a reference on a corresponding tomographic plane which is discriminated to be the focal plane.

18. A non-transitory computer-readable storage medium that stores a tomographic image generating program causing a computer to execute:

a step of acquiring a plurality of projection images corresponding to a plurality of radiation source positions, the plurality of projection images being generated by causing an imaging apparatus to perform tomosynthesis imaging in which a radiation source is moved relative to a detection surface of a radiation detector in order to emit radiation to a subject at the plurality of radiation source positions according to movement of the radiation source;

a step of reconstructing all or a part of the plurality of projection images to generate a tomographic image on each of a plurality of tomographic planes of the subject;

a step of detecting a plurality of feature point from a plurality of the tomographic images;

a step of discriminate whether the corresponding tomographic plane corresponding to the tomographic image in which each of the plurality of feature points is detected is a focal plane, and a step of deriving a positional shift amount between the plurality of projection images based on body movement of the subject with the feature point as a reference on a corresponding tomographic plane which is discriminated to be the focal plane.

\* \* \* \* \*